US008580749B2

(12) United States Patent
Wagner et al.

(10) Patent No.: US 8,580,749 B2
(45) Date of Patent: Nov. 12, 2013

(54) PEPTIDE-COATED CELL LOCALIZATION TO DISEASED OR DAMAGED TISSUES AND METHODS RELATED THERETO

(75) Inventors: Joseph Wagner, Shaker Heights, OH (US); Randell Young, Ellicott City, MD (US); David Fink, Baltimore, MD (US)

(73) Assignee: Cell Targeting, Inc., Alameda, CA (US)

( * ) Notice: Subject to any disclaimer, the term of this patent is extended or adjusted under 35 U.S.C. 154(b) by 332 days.

(21) Appl. No.: 12/795,195

(22) Filed: Jun. 7, 2010

(65) Prior Publication Data
US 2010/0310531 A1 Dec. 9, 2010

Related U.S. Application Data

(60) Provisional application No. 61/184,682, filed on Jun. 5, 2009.

(51) Int. Cl.
*A61K 38/08* (2006.01)

(52) U.S. Cl.
USPC .......... 514/21.7; 514/1.1; 514/21.8; 424/93.1

(58) Field of Classification Search
None
See application file for complete search history.

(56) References Cited

U.S. PATENT DOCUMENTS

| | | | |
|---|---|---|---|
| 6,303,573 B1 | 10/2001 | Ruoslahti et al. | |
| 6,316,256 B1 | 11/2001 | Tykocinski et al. | |
| 7,144,860 B2 | 12/2006 | Ruoslahti et al. | |
| 7,348,004 B2 | 3/2008 | Peters et al. | |
| 7,488,792 B2 | 2/2009 | Ruoslahti et al. | |
| 7,501,486 B2 | 3/2009 | Zhang et al. | |
| 2003/0045476 A1* | 3/2003 | Ruoslahti et al. | 514/16 |
| 2003/0198971 A1 | 10/2003 | Balint et al. | |
| 2004/0048370 A1 | 3/2004 | Dennis et al. | |
| 2004/0186056 A1 | 9/2004 | Ruoslahti et al. | |
| 2006/0160743 A1* | 7/2006 | Zhang et al. | 514/15 |
| 2006/0263336 A1 | 11/2006 | Caplan | |
| 2007/0269455 A1* | 11/2007 | Segal | 424/204.1 |
| 2008/0305101 A1 | 12/2008 | Ruoslahti et al. | |
| 2009/0036349 A1 | 2/2009 | Ruoslahti et al. | |
| 2009/0092548 A1* | 4/2009 | Ferrara et al. | 424/1.69 |
| 2009/0226372 A1 | 9/2009 | Ruoslahti et al. | |

FOREIGN PATENT DOCUMENTS

WO    WO 2008052046 A2 * 5/2008

OTHER PUBLICATIONS

Brinke et al., Palmitoylation and processing of the lipopeptide surfactant protein C, Biochimica et Biophysica Acta, vol. 1583 pp. 253-265 (2002).*
Zhang et al., Molecular Profiling of Heart Endothelial Cells, Circulation, v112 pp. 1601-1611 (Sep. 2005).*
Zhang et al. (Dynamic imaging of arginine-rich heart-targeted vehicles in a mouse model, Biomaterials, v29 pp. 1976-1988 (Feb. 2008)).*
Zhang et al., Dynamic Imaging of arginine-rich heart-targeted vehicles in a mouse model, Biomaterials 29: 1976-1988 (2008).*
Kean et al., Development of a peptide-targeted, myocardial ischemia-homing, mesenchymal stem cell, Journal of Drug Targeting (2012), 20(1):23-32.*
Banker, et al., A View to the Future, *Modern Pharmaceutics* (1979), Chapter 19, pp. 769-784, Marcel Dekker, Inc., New York and Basel.
Fitzpatrick, et al., Design, synthesis and in vitro testing of methotrexate carrier conjugates linked via oligopeptide spacers, *Anticancer Drug Design* (Jan. 1995), 10(1):1-9.
Goodman & Gilman, *The Pharmaceutical Basis of Therapeutics*, 6$^{th}$ Edition, MacMillan Publishing Co., New York (1980).
Lee, et al., Antibody Targeting of Stem Cells to Infarcted Myocardium, *Stem Cells* (Nov. 21, 2006), 25:712-717.
Ruel, et al., Angiogenic Protein Therapy, *Seminars in Thoracic and Cardiovascular Surgery* (Jul. 2003), 15(3):222-235.
Ware, et al., Angiogenesis in ischemic heart disease, *Nature Med.* (Feb. 1997); 3(2):158-164.
Conkright et al. (2001) JBC 276:14658, Secretion of Surfactant Protein C, an Integral Membrane Protein Requires the N-terminal Propeptide.
ATCC online Catalog; PC-12 cells.
Baneyx, Recombinant Protein Expression in *Escherichia coli*; (1999) Current Opinion in Biotechnology 10:411.
Furka et al.; General Method for Rapid Synthesis of Multicomponent Peptide Mixtures; (1990) Int J. Peptide Prot. Res. 37:487.
Latore et al.; Voltage Dependent Conductance Induced by Alamethicin-phospholipid Conjugates in Lipid Bilayers; (1981) Biophys. J. 36:803.
Vellinga et al.: Spacers Increase the Accessibility of Peptide Ligands Linked to the Carboxy Terminus of Adenovirus Minor Capsid Protein IX; (2004) J. of Virol. 78:3470.
Vance and Vance (Eds.); Lipid Assembly Into Cell Membranes; Biochemistry of Lipids, Lipoproteins and Membranes (4th Edition) ch. 17; St Elsevier Science B.V. (2002).
VOET and VOET; Biochemistry; John Wiley and Sons (1990).

* cited by examiner

*Primary Examiner* — Cecilia J Tsang
*Assistant Examiner* — Randall L Beane
(74) *Attorney, Agent, or Firm* — E. Stewart Mittler

(57) ABSTRACT

Embodiments of the present invention are directed to a coated cell comprising a therapeutic cell and a plurality of targeting complexes coating the therapeutic cell and each of said targeting complexes comprising a homing molecule, a lipid moiety, and a spacer having from about 1 to about 10 amino acids and covalently linking the homing molecule to the lipid moiety and wherein the lipid moiety is non-covalently attached to the therapeutic cell. In some embodiments, the therapeutic cell is a stem cell. Embodiments of the invention are directed to methods of coating a therapeutic cell. Embodiments of the invention are directed to methods of treating diseases of the vasculature.

20 Claims, 27 Drawing Sheets

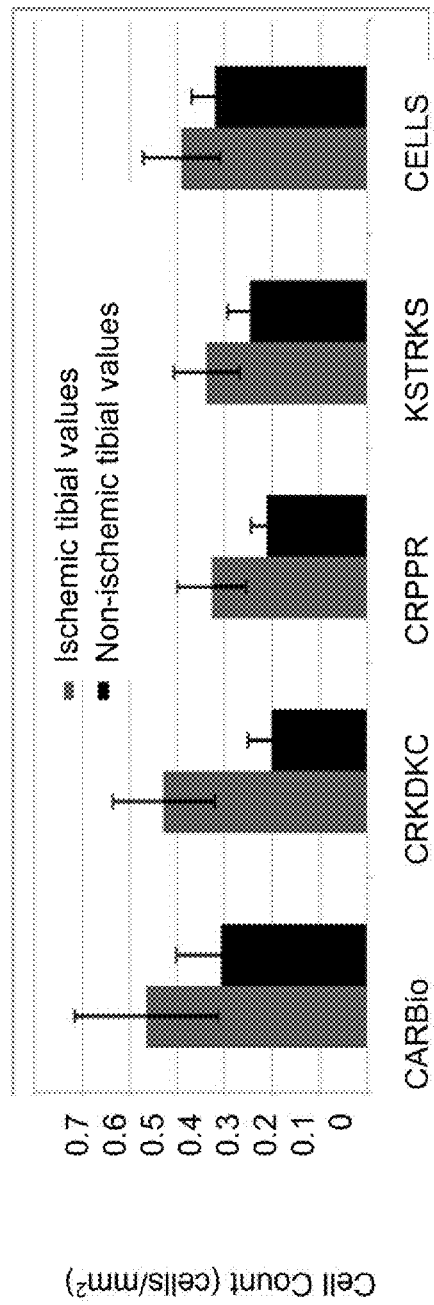
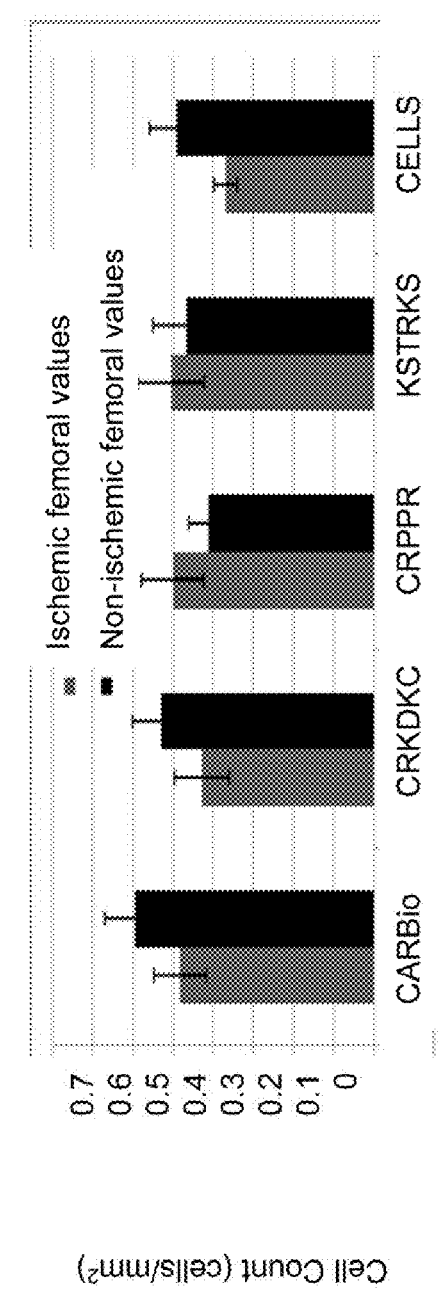
FIGURE 22A
FIGURE 22B

| Sequence | Homing Specificity | Reference |
|---|---|---|
| CRRETAWAC | α5β1 integrin in vitro | (Koivunen et al., 1994) |
| CRPPR | Heart – CRIP2 receptor | (Zhang et al., 2005) |
| CGLIQKNEC | Clot1, Blood clot | (Pilch et al., 2006) |
| CNAGESSKNC | Clot2, Blood clot | (Pilch et al., 2006) |
| CARSKNKDC | CAR, Wound | (Jarvinen and Ruoslahti, 2007) |
| CRKDKC | CRK, Wound | (Jarvinen and Ruoslahti, 2007) |
| KPGLNGLSSADPSSDWNAPAEEWG NWVDEDRASLLKSQEPISMDQKVSD DDKEKGEGALPTGKSK | Lung homing domain of metadherin | (Brown and Ruoslahti, 2004) |
| CREKA | Angiogenic vessels | (Essler and Ruoslahti, 2002) |
| CGKRK | Squamous cc | (Hoffman et al., 2003) |
| CAPGPSKSC | Atherosclerotic lesions of ApoE knockout mice | (Liu et al., 2003) |
| GRPARPAR | Positive control, Neuropilin-1 binding | (Teesalu et al., 2009) |
| CGGGGGGGC | Negative control | (Sugahara et al., 2009) |

FIGURE 24

| Peptide | 1st Screen | | | 2nd Screen | | | |
|---|---|---|---|---|---|---|---|
| | 1DMI N=3 | 3DMI N=3 | No MI N=3 | 1DMI N=3 | 3DMI N=3 | 7DMI N=1 | No MI N=3 |
| CRRETAWAC | 0.00 | 0.00 | 4.00 | 0.00 | 0.00 | 11.11 | 0.00 |
| CRPPR | 13.64 | 4.17 | 4.00 | 51.61 | 19.05 | 0.00 | 48.39 |
| CGLIIQKNEC | 4.55 | 2.08 | 0.00 | 0.00 | 0.00 | 0.00 | 3.23 |
| CNAGESSKNC | 9.09 | 6.25 | 0.00 | 0.00 | 4.76 | 0.00 | 0.00 |
| CARSKNKDC | 0.00 | 4.17 | 0.00 | 12.90 | 4.76 | 22.22 | 29.03 |
| CRKDKC | 4.55 | 8.33 | 0.00 | 0.00 | 0.00 | 0.00 | 0.00 |
| Metadherin | 0.00 | 0.00 | 0.00 | 0.00 | 4.76 | 0.00 | 0.00 |
| CREKA | 18.18 | 29.17 | 52.00 | 16.13 | 28.57 | 0.00 | 0.00 |
| CGKRK | 0.00 | 8.33 | 0.00 | 0.00 | 0.00 | 0.00 | 0.00 |
| CAPGPSKSC | 4.55 | 0.00 | 4.00 | 0.00 | 0.00 | 0.00 | 0.00 |
| GRPARPAR | 22.73 | 8.33 | 24.00 | 16.13 | 33.33 | 44.44 | 12.90 |
| CGGGGGGGC | 0.00 | 2.08 | 0.00 | 0.00 | 0.00 | 11.11 | 0.00 |
| KSTRKS | 9.09 | 25.00 | 8.00 | 3.23 | 4.76 | 11.11 | 6.45 |
| RIGRVLK | 9.09 | 2.08 | 4.00 | | | | |
| SKLGFF | 4.55 | 0.00 | 0.00 | | | | |

FIGURE 25

PEPTIDE-COATED CELL LOCALIZATION TO DISEASED OR DAMAGED TISSUES AND METHODS RELATED THERETO

CROSS-REFERENCE TO RELATED APPLICATIONS

This application claims the benefit of U.S. Provisional Application No. 61/184,682 entitled "Peptide Coated Cell Localization to Diseased or Damaged Tissues and Methods Related Thereto" filed Jun. 5, 2009, which is herein incorporated by reference in its entirety.

GOVERNMENT INTERESTS

Not Applicable

PARTIES TO A JOINT RESEARCH AGREEMENT

Not Applicable

INCORPORATION BY REFERENCE OF MATERIAL SUBMITTED ON A COMPACT DISC

Not Applicable

BACKGROUND

Not Applicable

BRIEF SUMMARY OF THE INVENTION

Embodiments of the invention provide molecular tools and methods for modifying cell surfaces with peptides that specifically target cells to diseased or damaged tissues. In particular, various aspects of the invention are directed to application-specific targeting complex coatings for a variety of indications.

Embodiments of the invention are directed to a targeting complex comprising a homing molecule, a lipid moiety, and a spacer having from about 1 to about 10 amino acids and covalently linking the homing molecule to the lipid moiety.

Embodiments of the invention are directed to a coated cell comprising a therapeutic cell and a plurality of targeting complexes coating the therapeutic cell and each of said targeting complexes comprising a homing molecule, a lipid moiety, and a spacer having from about 1 to about 10 amino acids and covalently linking the homing molecule to the lipid moiety.

Embodiments of the invention are directed to a pharmaceutical composition comprising a therapeutic cell and a plurality of targeting complexes coating the therapeutic cell and a pharmaceutically acceptable carrier, wherein each of the targeting complexes comprises a homing molecule, a lipid moiety, and a spacer having from about 1 to about 10 amino acids and covalently linking the homing molecule to the lipid moiety.

Embodiments of the invention are directed to a method of coating a cell comprising incubating about 10 µg/mL to about 100 µg/mL of a targeting complex, comprising a homing molecule and a lipid moiety, with a cell to be coated. In certain embodiments, the method comprises a targeting complex which further comprises a spacer, wherein the spacer comprises from about 1 to about 10 amino acids. In certain embodiments of the present invention, the incubating step is performed for about 5 to about 120 minutes. In certain embodiments of the present invention, the incubating step further comprises shaking the targeting complex and the cell to be coated. In certain embodiments of the present invention, the incubating step is carried out at a temperature from about 15° C. to about 45° C. In certain embodiments of the present invention, the method of coating a cell further comprises washing the coated cell. In certain embodiments of the present invention, the method of coating a cell further comprises washing the coated cell with Tyrodes solution, TBS, BES, ADA, PIPES, MES, MOPS, TAPS, TSS, NEB, Tris-HCl, HEPES, DMEM, FBS, MEM, CMRL media, Click's Media, BME, 293 Cell Media, CHO Cell Media, MDCK Media, MCDB Media, GMEM, IMEM, McCoy's SA Media, Williams' media, VERO Cell media, Liebovitz L15 Media, Iscove's Media, Ham's F-10, and Ham's F-20 media, RPMI media and PBS solution. In certain embodiments of the present invention, the method of coating a cell further comprises resuspending the coated cell.

Embodiments of the invention are directed to a method of treating a cardiovascular disease in a subject in need thereof comprising administering to the subject a coated cell comprising a therapeutic cell coated with a plurality of targeting complexes comprising a homing molecule, a lipid moiety, and a spacer having from about 1 to about 10 amino acids and covalently linking the homing molecule to the lipid moiety.

In certain embodiments of the invention, the homing molecule is a homing peptide. In certain embodiments of the invention, the homing molecule is selected from a group consisting of CRPPR (SEQ ID NO: 1), CRRETAWAC (SEQ ID NO: 2), CGLIIQKNEC (SEQ ID NO: 3), CNAGESSKNC (SEQ ID NO: 4), CARSKNKDC (SEQ ID NO: 5), CRKDKC (SEQ ID NO: 6), KPGLNGLSSADPSSDWNAPAEEWGN-WVDEDRASLLKSQEPISNDQKVSDDD KEKGE-GALPTGKSK (SEQ ID NO: 7), CREKA (SEQ ID NO: 8), CGKRK (SEQ ID NO: 9), CAPGPSKSC (SEQ ID NO: 10), GRPARPAR (SEQ ID NO: 11), CGGGGGGGC (SEQ ID NO. 12), KSTRKS (SEQ ID NO: 14), RIGRVLK (SEQ ID NO. 15), SKLGFF (SEQ ID NO. 16), GGGVFWQ (SEQ ID NO. 17), HGRVRPH (SEQ ID NO. 18), VVLVTSS (SEQ ID NO. 19), CLHRGNSC (SEQ ID NO. 20), CRSWNKAD-NRSC (SEQ ID NO. 21), CARPAR (SEQ ID NO. 22), and CPKRPR (SEQ ID NO. 23), or a functionally equivalent modification thereof. In certain embodiments, the homing molecule comprises a homing peptide that selectively homes to vasculature.

In certain embodiments of the invention, the lipid moiety is selected from the group consisting of a palmitoyl moiety, a myristoyl moiety, a margaroyl moiety, a stearoyl moiety, an arachidoyl moiety, an acetyl moiety, a butyryl moiety, a hexanoyl moiety, an octanoyl moiety, a decnoyl moiety, a lauroyl moiety, a palmitoleoyl moiety, a behenoyl moiety, and a lignoceroyl moiety. In certain embodiments of the present invention, the lipid moiety is palmitic acid. In certain embodiments of the present invention, the lipid moiety is integrated into the lipid bilayer of the cell membrane of the therapeutic cell. In certain embodiments of the present invention, the lipid moiety is intercalated into the lipid bilayer of the cell. In certain embodiments, the lipid moiety is non-covalently attached to the therapeutic cell.

In certain embodiments of the present invention, the spacer comprises from about 1 to about 5 amino acids.

In certain embodiments of the invention, the therapeutic cell can include any potentially therapeutic cell. In certain embodiments of the present invention, the therapeutic cell is a stem cell. In certain embodiments of the present invention, the stem cell is selected from a group consisting of a multipotent adult progenitor cell, a mesenchymal stem cell and a hematopoietic stem cell. In certain embodiments of the present invention, the coated cell has a coating comprising about 0.01 µM to 1 mM of the homing molecule.

In some embodiments, the homing molecule has an affinity to receptors in repairing vascular tissue, tissue undergoing neovascularization, tissues suffering from ischemia, transplant tissue and wounds in general, among others. In some embodiments, the homing molecule targets tissues including, but not limited to, vasculature, wounds, bone marrow, tumors, heart, lung, muscle, liver, spleen and kidney.

DESCRIPTION OF DRAWINGS

For a fuller understanding of the nature and advantages of the present invention, reference should be had to the following detailed description taken in connection with the accompanying drawings, in which:

FIG. 22A illustrates a summary of Mean Cell Densities observed in the tibial (calf) sections of the ischemic and non-ischemic legs. Mean±SEM for N≥15.

FIG. 22B illustrates a summary of Mean Cell Densities observed in the femoral (thigh) sections of the ischemic and non-ischemic legs. Mean±SEM for N≥15.

FIG. 24 illustrates the phage peptide screen, sequences and homing specificities.

FIG. 25 illustrates the phage titer from 1, 3, and 7 day post-MI as percentages of total analyzed from heart tissue.

DETAILED DESCRIPTION

Figure 1:
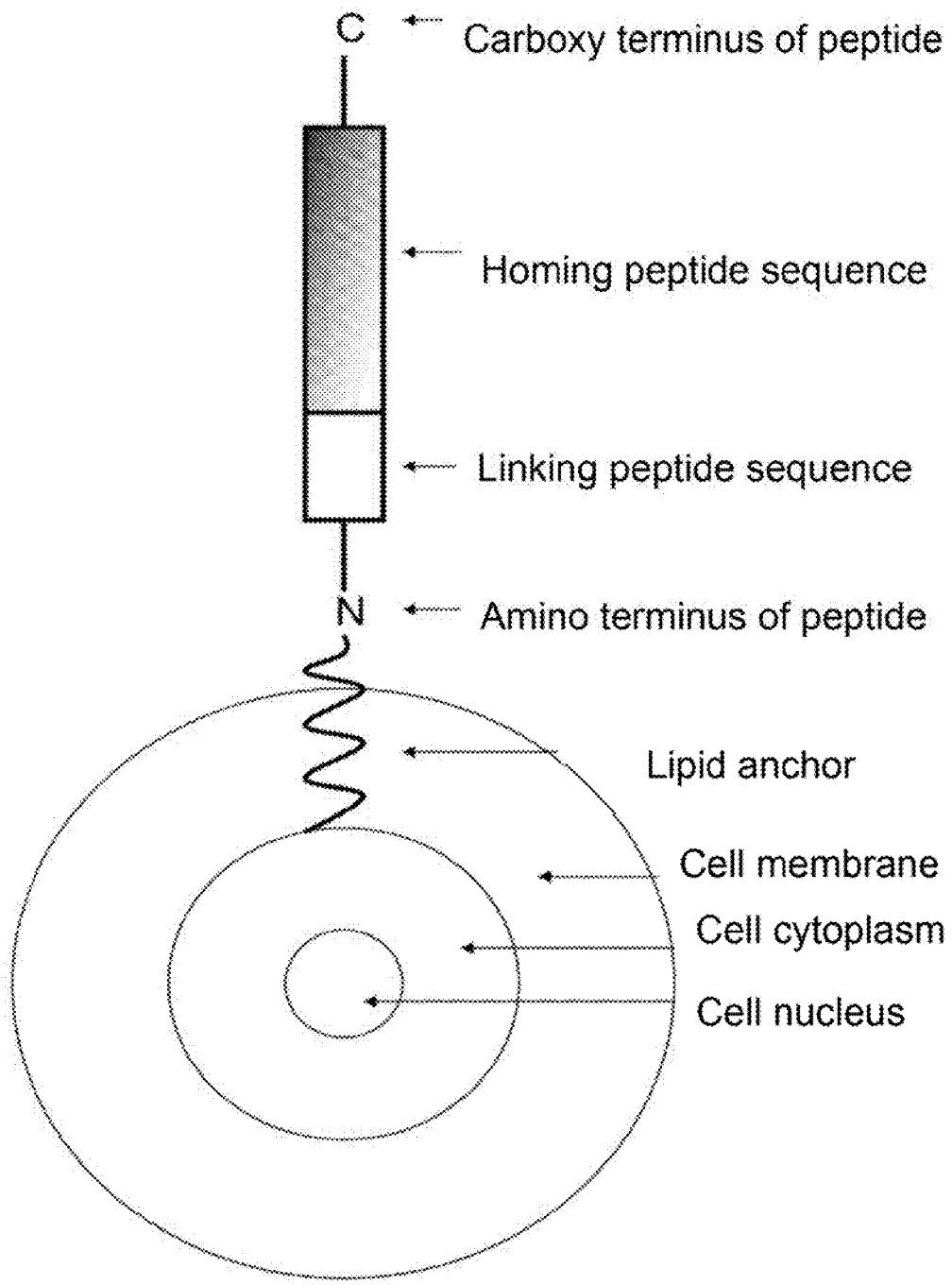
FIG. 1 illustrates a schematic of a targeting complex according to one embodiment of the present invention. The schematic is not to scale and although the schematic depicts a single lipidated homing molecule, in fact many thousands, if not millions, of lipidated homing molecules may be associated with each cell.

Before the present compositions and methods are described, it is to be understood that this invention is not limited to the particular processes, compositions, or methodologies described, as these may vary. It is also to be understood that the terminology used in the description is for the purpose of describing the particular versions or embodiments only, and is not intended to limit the scope of the present invention which will be limited only by the appended claims. Unless defined otherwise, all technical and scientific terms used herein have the same meanings as commonly understood by one of ordinary skill in the art. Although any methods and materials similar or equivalent to those described herein can be used in the practice or testing of embodiments of the present invention, the preferred methods, devices, and materials are now described. All publications mentioned herein are incorporated by reference in their entirety. Nothing herein is to be construed as an admission that the invention is not entitled to antedate such disclosure by virtue of prior invention.

It must also be noted that as used herein and in the appended claims, the singular forms "a", "an", and "the" include plural reference unless the context clearly dictates otherwise. Thus, for example, reference to a "homing molecule" is a reference to one or more homing molecules and equivalents thereof known to those skilled in the art, and so forth.

As used herein, the term "about" means plus or minus 10% of the numerical value of the number with which it is being used. Therefore, about 50% means in the range of 45%-55%.

"Administering" when used in conjunction with a coated cell means to administer a coated cell directly into or onto a target tissue or to administer a coated cell to a patient whereby the coated cell positively impacts the tissue to which it is targeted. Thus, as used herein, the term "administering", when used in conjunction with a coated cell, can include, but is not limited to, providing a coated cell into or onto the target tissue; providing a coated cell systemically to a patient by, e.g., intravenous injection whereby the therapeutic reaches the target tissue; providing a coated cell in the form of the encoding sequence thereof to the target tissue (e.g., by so-called gene-therapy techniques) or local administration of a coated cell. "Administering" a composition may be accomplished by oral administration, intravenous injection, intraperitoneal injection, intramuscular injection, subcutaneous injection, transdermal diffusion or electrophoresis, local injection, extended release delivery devices including locally implanted extended release devices such as bioerodible or reservoir-based implants, as protein therapeutics or as nucleic acid therapeutic via gene therapy vectors or by any of these methods in combination with other known techniques. Such combination techniques include heating, radiation and ultrasound.

The term "animal" or "subject" as used herein includes, but is not limited to, humans and non-human vertebrates such as wild, domestic and farm animals.

The term "inhibiting" includes the administration of a coated cell of the present invention to prevent the onset of the symptoms, alleviating the symptoms, or eliminating the disease, condition or disorder.

By "pharmaceutically acceptable", it is meant the carrier, diluent or excipient must be compatible with the other ingredients of the formulation and not deleterious to the recipient thereof.

As used herein, the term "therapeutic agent" means an agent utilized to treat, combat, ameliorate, prevent or improve an unwanted condition or disease of a patient. In part, embodiments of the present invention are directed to the treatment of cardiopathies, cardiovascular diseases and diseases that involve vasculature. In some embodiments, the therapeutic agent may be any potentially therapeutic cell. In some embodiments, the therapeutic agent may be a stem cell.

A "therapeutically effective amount" or "effective amount" of a composition is a predetermined amount calculated to achieve the desired effect, i.e., to inhibit, block, or reverse the activation, migration, or proliferation of cells. The activity contemplated by the present methods includes both medical therapeutic and/or prophylactic treatment, as appropriate. The specific dose of a targeting complex administered according to this invention to obtain therapeutic and/or prophylactic effects will, of course, be determined by the particular circumstances surrounding the case, including, for example, the targeting complex administered, the route of administration, and the condition being treated. It will be understood that the effective amount administered will be determined by the physician in the light of the relevant circumstances including the condition to be treated, the choice of targeting complex to be administered, and the chosen route of administration. A therapeutically effective amount of targeting complex of this invention is typically an amount such that when it is administered in a physiologically tolerable excipient composition, it is sufficient to achieve an effective systemic concentration or local concentration in the targeted tissue.

The terms "treat," "treated," or "treating" as used herein refers to both therapeutic treatment and prophylactic or preventative measures, wherein the object is to prevent or slow down (lessen) an undesired physiological condition, disorder or disease, or to obtain beneficial or desired clinical results. For the purposes of this invention, beneficial or desired clinical results include, but are not limited to, alleviation of symptoms; diminishment of the extent of the condition, disorder or disease; stabilization (i.e., not worsening) of the state of the condition, disorder or disease; delay in onset or slowing of the progression of the condition, disorder or disease; amelioration of the condition, disorder or disease state; and remission (whether partial or total), whether detectable or undetectable, or enhancement or improvement of the condition, disorder or disease. Treatment includes eliciting a clinically significant response without excessive levels of side effects. Treatment also includes prolonging survival as compared to expected survival if not receiving treatment.

Generally speaking, the term "tissue" refers to any aggregation of similarly specialized cells that are united in the performance of a particular function.

The term "homing molecule" as used herein, means any molecule that selectively localizes to and associates with a particular tissue or cell type in preference to other tissue or cell types. In various embodiments, such homing molecules may be used to deliver cargo molecules such as, for example, a therapeutic cell, to the particular "target tissue" or "target cells" with which the homing molecule selectively associates and any vasculature associated with the tissue or cells. For example, certain embodiments are directed to homing molecules that selective associate with cardiac or heart tissue. Thus, cargo associated with such homing molecules may be delivered to portions of the cardiovascular system. Selective localization is generally characterized by the homing molecule exhibiting an at least a two-fold greater affinity for a target tissue or target cell type as compared to other non-targeted tissues or cell types. In various embodiments, a homing molecule can be characterized by 5-fold, 10-fold, 20-fold or more preferential affinity for a target tissue or cell type. It is understood that a homing molecule can localize to and associate with, in part, to vasculature or tissue outside the target or to a small population of cells outside of the target in addition to selectively localizing to the target.

The term "homing peptide" refers to a particular type of homing molecule that is a peptide or peptidomimetic that selectively localizes and associates with a target tissue or cell type in preference to other non-targeted tissue or cell type and portions of the vasculature associated therewith. The term "targeting complex" means a homing molecule that is covalently attached to a lipid moiety. In some embodiments, the targeting complex may further include a spacer.

"Optional" or "optionally" may be taken to mean that the subsequently described structure, event or circumstance may or may not occur, and that the description includes instances where the event occurs and instances where it does not.

Some embodiments of the invention are directed to a targeting complex including a homing molecule, a lipid moiety, and a spacer covalently binding the homing molecule to the lipid moiety. In some embodiments, the spacer may include from about 1 to about 10 amino acids. In some embodiments, the homing molecule may be a peptide. Other embodiments are directed to cells coated with a plurality of targeting complexes. In such embodiments, each of said targeting complexes may include a homing molecule, a lipid moiety, and a spacer covalently linking the homing molecule to the lipid moiety, and in certain embodiments, the cell may be a therapeutic cell such as, for example, a stem cell. The targeting complex can associate with the cell through non-covalent interactions with the cell. For example, in some embodiments as illustrated in FIG. 1, the lipid moiety may intercalate into the lipid bi-layer of the cell membrane anchoring the targeting complex to the cell and allowing the homing molecule to be presented on the outer surface of the cell. This arrangement allows the homing molecule, which is capable of preferentially associating with a target tissue or cell type, to effectively carry the cell, or other cargo, to the target tissue and any portion of the vasculature associated therewith. Further embodiments are directed to methods for coating cells (cell painting or cell coating) with a targeting complex including a homing molecule, a lipid moiety, and a spacer covalently linking the homing molecule to the lipid moiety.

Without wishing to be bound by theory, the use of the targeting complex of various embodiments to coat a cell has several advantages to methodologies in the prior art. For example, intercalation of the lipid moiety of the homing molecule into the lipid bi-layer of the cell membrane is a transient modification to the cell and, as such, should not perturb the cell or interfere with the normal processes of the cell. Thus, use of the targeting complexes of the invention may avoid the some problems associated with producing a genetically altered cells such as regulatory challenges, transfection efficiency issues, mutation causing integration events, unknown changes in cell physiology, and long-term antigenicity of transfected cells. Furthermore, lipid integration into the cell membrane can be applied to any cell type, and peptide discovery and synthesis are possible against a wide range of target tissues. For example, development of novel peptide ligands specific to distinct portions of the vasculature or portions of a target organ may allow greater control over delivery. This control could further be enhanced by using two or more different targeting complexes having different homing molecules on a single cell. Additionally, mass production of the homing molecules may be considerably cheaper than that of an antibody.

In certain embodiments, the targeting molecule may include a homing molecule that selectively associates with vascular tissue, tissue undergoing neovascularization, ischemic tissues, tumors, or wounds, among others. In particular embodiments, the homing molecule may be substantially inert. By "inert" is meant that administration of the homing molecule creates substantially no physiological effect on the target tissue or cells upon contact with the homing molecule or, more generally, patient to whom the homing molecule is administered. For example, the homing molecule may not induce any form of cellular transformation or produce an inflammatory response when contacting the target tissue.

In various embodiments, the homing molecule of the targeting complex may be a peptide, and any peptide having an affinity for a particular tissue or cell type over other tissues or cell types known in the art may be used in such embodiments. For example, in some embodiments, the peptide homing molecule can include, but are not limited to, CRPPR (SEQ ID NO: 1), CRRETAWAC (SEQ ID NO: 2), CGLIIQKNEC (SEQ ID NO: 3), CNAGESSKNC (SEQ ID NO: 4), CARSKNKDC (SEQ ID NO: 5), CRKDKC (SEQ ID NO: 6), KPGLNGLSSADPSSDWNAPAEEWGNWVD-EDRASLLKSQEPISNDQKVSDDDKEKGEG ALPT-GKSK (SEQ ID NO: 7), CREKA (SEQ ID NO: 8), CGKRK (SEQ ID NO: 9), CAPGPSKSC (SEQ ID NO: 10), GRPAR-PAR (SEQ ID NO: 11), CGGGGGGGC (SEQ ID NO. 12), and combinations, functional equivalents, and mimetics thereof. The homing specificities of these peptides are listed in FIG. 24. In other embodiments, the peptide homing molecule can include, but are not limited to, KSTRKS (SEQ ID NO: 14), RIGRVLK (SEQ ID NO. 15), SKLGFF (SEQ ID NO. 16), GGGVFWQ (SEQ ID NO. 17), HGRVRPH (SEQ ID NO. 18), VVLVTSS (SEQ ID NO. 19), CLHRGNSC (SEQ ID NO. 20), CRSWNKADNRSC (SEQ ID NO. 21), CARPAR (SEQ ID NO. 22), and CPKRPR (SEQ ID NO. 23), and combinations, functional equivalents, and mimetics thereof.

An isolated peptide or peptidomimetic can be, without limitation, cyclic or otherwise conformationally constrained. As used herein in reference to a molecule, the term "conformationally constrained" means a molecule, such as a peptide or peptidomimetic, in which the three-dimensional structure is maintained substantially in one spatial arrangement over time. Conformationally constrained molecules can have improved properties such as increased affinity, metabolic stability, membrane permeability or solubility. Methods of conformational constraint are well known in the art and include, without limitation, cyclization.

As used herein in reference to a peptide or peptidomimetic, the term "cyclic" refers to a structure including an intramolecular bond between two non-adjacent amino acids or amino acid analogs. The cyclization can be affected through a covalent or non-covalent bond. Intramolecular bonds include, but are not limited to, backbone to backbone, side-chain to backbone, and side-chain to side-chain bonds. Methods of cyclization include, without limitation, formation of a disulfide bond between the side-chains of non-adjacent amino acids or amino acid analogs; formation of a lactam bond, for example, between a side-chain group of one amino acid or analog thereof to the N-terminal amine of the amino-terminal residue; and formation of lysinonorleucine and dityrosine bonds.

The targeting molecules of embodiments may include any soluble lipid known in the art that can covalently bind to the N-terminus of a spacer and can be manipulated to achieve membrane integration can be used in embodiments. The lipid moiety of various embodiments may be saturated, unsaturated, or polyunsaturated and may include any number of carbons. For example, in some embodiments, the lipid moiety may include an aliphatic chain of from about 4 to about 30 carbons, and in other embodiments, the lipid moiety may include an aliphatic chain having from about 10 to about 24 carbons. In still other embodiments, the lipid moiety may include two or more aliphatic chains of about 4 to about 30 carbons or about 10 to about 24 carbons linked through, for example, a glyceride. In certain embodiments, the lipid moiety may have a carboxylic acid terminus and the spacer may be covalently linked to the lipid moiety through the carboxylic acid terminus. In some embodiments, the lipid moiety may be derived from, for example, a glycolipid, a glycerolipid, a phospholipid and a cholesterol, and spacer may be covalently linked to the lipid through the sugar, phosphate, or cholesterol associated with these lipid moieties. In particular embodiments, the lipid moiety may be a palmitoyl moiety, myristoyl moiety, margaroyl moiety, stearoyl moiety, arachidoyl moiety, acetyl moiety, butytyl moiety, hexanoyl moiety, octanoyl moiety, decnoyl moiety, lauroyl moiety, palmitoleoyl moiety, behenoyl moiety, or lignoceroyl moiety, and in some embodiments, the lipid moiety may be palmitic acid.

In some embodiments, the targeting complex may further include a spacer that covalently links the homing molecule with the lipid moiety by binding the homing molecule on one end and to the lipid moiety on the other end. Without being bound by theory, the spacer may improve the hydrophilicity of the homing molecule, and in embodiments in which the homing molecule is a peptide, the spacer may allow the conformation of the homing peptide to be maintained during intercalation of the targeting complex and delivery of the cell. In certain embodiments, the spacer may be a peptide of one or more amino acids. For example, in some embodiments, the spacer may be a peptide of from about 1 to about 10 amino acids or from about 1 to about 5 amino acids. In other embodiments, the spacer may be a single amino acid or a peptide of 2 amino acids, 3 amino acids, 4 amino acids, 5 amino acids, 6 amino acids, 7 amino acids, 8 amino acids, 9 amino acids, and 10 amino acids. The peptide spacers of embodiments are not limited by the amino acid sequence of the spacer. In particular embodiments, the spacer may be a tri-peptide having the amino acid sequence asparagine-serine-lysine (NSK) or asparagine-lysine-serine (NKS).

In some embodiments, the targeting complex described herein may include a homing molecule covalently linked to a lipid moiety. In other embodiments, the targeting complex described herein may include a homing molecule, a lipid moiety, and a spacer covalently linking the homing molecule to the lipid moiety, and in certain embodiments, the spacer may have from about 1 to about 10 amino acids. In still other embodiments, the coated cell described herein may include a therapeutic cell coated with a targeting molecule including a homing molecule, a lipid moiety, and a spacer having from about 1 to about 10 amino acids covalently linking the homing molecule to the lipid moiety. In such embodiments, the lipid moiety may be non-covalently attached to the therapeutic cell.

In some embodiments, the targeting complex may be associated with a cell, and in particular embodiments, the cell may be a potentially therapeutic cell such as, for example, a stem cell. As such, embodiments of the invention include targeting complexes associated with cells such as, but not limited to, multipotent adult progenitor cells (MAPCs), mesenchymal stem cells (MSCs), and hematopoietic stem cells (HSCs). Some such therapeutic cells may have an inherent capacity to localize to a target tissue. For example, MSCs have an inherent capacity to localize in ischemic heart tissue. The targeting complex may increase this capacity to localize increasing the percentage of cells that localize in damaged tissue and reducing the cell dose needed.

The concentration of the targeting complex on the surface of the coated cell may vary among embodiments, but is generally sufficient to allow the cell to be delivered to the desired target tissue based on the homing molecule. Without wishing to be bound by theory, the concentration of targeting complex may be reduced on cells having an inherent affinity for the target tissue. As such, in some embodiments, the concentration of targeting complex incorporated into the cell may be from about 0.001 µM to 1 mM, and in other embodiments, the concentration of targeting complex incorporated into the cell may be from about 0.01 µM to 500 µM of the homing molecule.

Some embodiments are directed to methods of coating a cell with a targeting complex including a homing molecule covalently bonded to a spacer having from about 1 to about 10 amino acids. In some embodiments, a therapeutic agent can be a small organic molecule that, upon binding to a target cell via a homing molecule is internalized by the cell where it can effect its function. In other embodiments, therapeutic agents include viral gene therapy vectors and viruses; nucleic acid molecules and oligonucleotides including antisense and dominant negative molecules; polypeptides and peptides; and small molecule drugs.

In some embodiments, the therapeutic agent can include any natural or non-natural material such as an organic chemical, radionuclide, nucleic acid molecule or oligonucleotide, polypeptide, or peptidomimetic. In other embodiments, the therapeutic agent may include a diagnostic agent or imaging agent; or a tag or insoluble support. In still other embodiments, the therapeutic agent may further include viral gene therapy vectors, viruses, nucleic acid molecules, oligonucleotides, polypeptides, peptidomimetics, small molecule drugs, cells, liposomes, microcapsules, microspheres, and micropumps, and other chambered micro-devices that can be used as a delivery system for the therapeutic agent.

Angiogenesis-based therapy using a therapeutic agent that stimulates new blood vessel formation (angiogenesis) can be useful for treating a cardiovascular disease. Angiogenic agents can be useful for treating, without limitation, ischemic heart disease including chronic myocardial ischemia and acute myocardial infarction. Many patients with severe vascular disease that are not candidates for mechanical revascularization can benefit from angiogenesis-based therapy, including those patients with occlusion of vessels too small to be bypassed, those without conduits and those who are not surgical candidates because of concomitant disease. Thus, in some embodiments, a molecule that selectively localizes to heart vasculature can be linked to an angiogenic agent and delivered to a subject, thereby stimulating angiogenesis and alleviating the cardiovascular disease. An angiogenic agent useful in embodiments of the invention also can be a naturally occurring angiogenic growth factor or cytokine that induces or promotes angiogenesis by stimulating endothelial cell growth or migration. Angiogenic agents useful in embodiments of the invention comprise, without limitation, isoforms of vascular endothelial growth factor (VEGF) such as VEGF-A, including $VEGF_{121}$ and $VEGF_{165}$, and forms of fibroblast growth factor including, but not limited to, forms of FGF-1 and FGF-2 (Ruel and Selike, *Sem. Thor. Cardiovasc. Surg.*

15:222-235 (2003). Angiogenic agents and other therapeutic agents of the invention can be delivered as protein therapeutics or as nucleic acid therapeutic via gene therapy vectors.

Further embodiments of the invention are directed to methods for coating a cell including the step of incubating a targeting complex, including a homing molecule, a lipid moiety, and a spacer covalently linking the homing molecule to the lipid moiety, with a cell to be coated. The methods of particular embodiments may include only the step of incubating cells to be coated with the targeting complex. As such, the invention provides a one step method for coating (or painting) cells with a targeting complex.

The incubation may be carried out in any liquid buffer known in the art that is capable of sustaining living cells, and the skilled artisan can choose factors such as, pH, salinity, and the like based on, for example, the type of cells being coated. In some embodiments, the buffer in which the coating method is carried out may be, without limitation, Tyrodes solution, Tris Buffered Saline (TBS) solution, BES, ADA, PIPES, MES, MOPS, TAPS, TSS, NEB, Tris-HCl, HEPES, Hank's balanced salt solution, Phosphate Buffered Saline (PBS) solution or any other type of buffer which is compatible with living cells.

In some embodiments, the number of cells being coated may encompass from about 1,000 cells/mL to about 3 million cells/mL. In other embodiments, the number of cells being coated may encompass from about 10,000 cells/mL to about 3 million cells/mL, from about 100,000 cells/mL to about 2 million cells/mL, from about 200,000 cells/mL to about 1 million cells/mL, or from about 200,000 cells/mL to about 750,000 cells/mL.

The amount of targeting complex provided to the buffer may vary among embodiments and may vary depending, for example, on the number of cells being coated, the size of the cells, the density of the coating to be applied to the cells and the like. For example, in a method for coating mesenchymal stem cells at a concentration of about 500,000 cells/mL, from about 10 µg/mL to about 100 µg/mL of the targeting complex may be provided to the buffer during incubation. In other embodiments, from about 10 µg/mL to about 60 µg/mL of the targeting complex may be provided to the buffer during incubation, and in still other embodiments, from about 15 µg/mL to about 55 µg/mL, about 20 µg/mL, or about 50 µg/mL may be provided to the buffer during incubation.

The time required for sufficient coating to occur may also vary among embodiments and may depend upon, for example, the type of cells being coated, the number of cells being coated, and such. For example, in some embodiments, incubating may be carried out for about 5 to about 120 minutes, and in other embodiments, incubating may be carried out for about 5 to about 60 minutes, about 5 to about 30 minutes, or about 5 to about 10 minutes.

In certain embodiments, the incubating step further include shaking the targeting complex and the cell to be coated. Shaking can be carried out based on the knowledge of the skilled artisan and can be carried out at sufficient speed to allow adequate mixing and contact between the targeting complex and the cells to be coated but not carried out at a speed that will damage the cells.

In some embodiments, the incubating step may be carried out at a temperature from about 5° C. to about 45° C., and in other embodiments, the incubating step may be carried out at a temperature from about 15° C. to about 40° C. or about 30° C. to about 40° C. In certain embodiments, the incubating step is carried out at a temperature about 37° C.

The methods of various embodiments may include any number of additional steps carried out after the coating process is completed. For example, in certain embodiments, the method of coating a cell further include the steps washing the coated cell, and in some embodiments, washing the coated cells may be carried out with, without limitation, Tyrodes solution, Tris Buffered Saline (TBS) solution, BES, ADA, PIPES, MES, MOPS, TAPS, TSS, NEB, Tris-HCl, HEPES, Hank's balanced salt solution, Phosphate Buffered Saline (PBS) solution or any other type of buffer which is compatible with living cells. In some embodiments of the present invention, the step of washing the coated cell may be carried out with, without limitation, Dulbecco's Modified Eagle's Medium (DMEM), Fetal Bovine Serum (FBS), Minimum Essential Medium Eagle (MEM), Connaught Medical Research Laboratories (CMRL) media, Click's Media, Basal Medium Eagle (BME), 293 Cell Media, CHO Cell Media, MDCK Media, MCDB Media, Glasgow's MEM (GMEM), Improved MEM (IMEM), McCoy's SA Media, Williams' media, VERO Cell media, Liebovitz L15 Media, Iscove's Media, Ham's F-10, and Ham's F-20 media, Roswell Park Memorial Institute (RPMI) media, among others. In some embodiments, the method further comprises fixing the cell solution with formalin. In some embodiments, the method further comprises trypsinizing the therapeutic cells before incubation. In particular embodiments, the method of coating a cell may further include resuspending the coated cells in a buffer solution or other cell medium following the step of washing the cells.

The methods of various embodiments may result in a concentration of the targeting complex on the surface of the coated cell that is sufficient to allow the cell to be delivered to the desired target tissue based on the homing molecule. In some embodiments, the concentration of targeting complex incorporated into the cell following the coating methods described above may be from about 0.001 µM to 1 mM, and in other embodiments, the concentration of targeting complex incorporated into the cell may be from about 0.01 µM to 500 µM of the homing molecule.

Embodiments of the invention are directed to a pharmaceutical composition comprising a therapeutic cell and a plurality of targeting complexes coating the therapeutic cell and a pharmaceutically acceptable carrier or diluent, wherein each of the targeting complexes comprises a homing molecule, a lipid moiety, and a spacer covalently linking the homing molecule to the lipid moiety. In some embodiments, the spacer may have from about 1 to about 10 amino acids, and in other embodiments, the lipid moiety is non-covalently attached to the therapeutic cell.

Thus, modes of administration for the targeting complex of the present invention (either alone or in combination with other pharmaceuticals) can be, but are not limited to, sublingual, injectable (including short-acting, depot, implant and pellet forms injected subcutaneously or intramuscularly), or by use of vaginal creams, suppositories, pessaries, vaginal rings, rectal suppositories, intrauterine devices, and transdermal forms such as patches and creams.

Specific modes of administration will depend on the indication. The selection of the specific route of administration and the dose regimen is to be adjusted or titrated by the clinician according to methods known to the clinician in order to obtain the optimal clinical response. The amount of targeting complex to be administered is that amount which is therapeutically effective. The dosage to be administered will depend on the characteristics of the subject being treated, e.g., the particular animal treated, age, weight, health, types of concurrent treatment, if any, and frequency of treatments, and can be easily determined by one of skill in the art (e.g., by the clinician).

Pharmaceutical formulations containing the targeting complex of the present invention and a suitable carrier can be solid dosage forms which include, but are not limited to, tablets, capsules, cachets, pellets, pills, powders and granules; topical dosage forms which include, but are not limited to, solutions, powders, fluid emulsions, fluid suspensions, semi-solids, ointments, pastes, creams, gels and jellies, and foams; and parenteral dosage forms which include, but are not limited to, solutions, suspensions, emulsions, and dry powder; comprising an effective amount of a polymer or copolymer of the present invention. It is also known in the art that the active ingredients can be contained in such formulations with pharmaceutically acceptable diluents, fillers, disintegrants, binders, lubricants, surfactants, hydrophobic vehicles, water soluble vehicles, emulsifiers, buffers, humectants, moisturizers, solubilizers, preservatives and the like. The means and methods for administration are known in the art and an artisan can refer to various pharmacologic references for guidance. For example, Modern Pharmaceutics, Banker & Rhodes, Marcel Dekker, Inc. (1979); and *Goodman & Gilman's The Pharmaceutical Basis of Therapeutics,* 6th Edition, MacMillan Publishing Co., New York (1980) can be consulted.

The compositions and coated cells of the present invention can be formulated for parenteral administration by injection, e.g., by bolus injection or continuous infusion. The compositions and coated cells can be administered by continuous infusion subcutaneously over a period of about 15 minutes to about 24 hours. Formulations for injection can be presented in unit dosage form, e.g., in ampoules or in multi-dose containers, with an added preservative. The compositions can take such forms as suspensions, solutions or emulsions in oily or aqueous vehicles, and can contain formulatory agents such as suspending, stabilizing and/or dispersing agents.

For oral administration, the compositions and coated cells can be formulated readily by combining these targeting complex with pharmaceutically acceptable carriers well known in the art. Such carriers enable the targeting complex of the invention to be formulated as tablets, pills, dragees, capsules, liquids, gels, syrups, slurries, suspensions and the like, for oral ingestion by a patient to be treated. Pharmaceutical preparations for oral use can be obtained by adding a solid excipient, optionally grinding the resulting mixture, and processing the mixture of granules, after adding suitable auxiliaries, if desired, to obtain tablets or dragee cores. Suitable excipients include, but are not limited to, fillers such as sugars, including, but not limited to, lactose, sucrose, mannitol, and sorbitol; cellulose preparations such as, but not limited to, maize starch, wheat starch, rice starch, potato starch, gelatin, gum tragacanth, methyl cellulose, hydroxypropylmethyl-cellulose, sodium carboxymethylcellulose, and polyvinylpyrrolidone (PVP). If desired, disintegrating agents can be added, such as, but not limited to, the cross-linked polyvinyl pyrrolidone, agar, or alginic acid or a salt thereof such as sodium alginate.

Dragee cores can be provided with suitable coatings. For this purpose, concentrated sugar solutions can be used, which can optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments can be added to the tablets or dragee coatings for identification or to characterize different combinations of active targeting complex doses.

Pharmaceutical preparations which can be used orally include, but are not limited to, push-fit capsules made of gelatin, as well as soft, sealed capsules made of gelatin and a plasticizer, such as glycerol or sorbitol. The push-fit capsules can contain the active ingredients in admixture with filler such as, e.g., lactose, binders such as, e.g., starches, and/or lubricants such as, e.g., talc or magnesium stearate and, optionally, stabilizers. In soft capsules, the active targeting complex can be dissolved or suspended in suitable liquids, such as fatty oils, liquid paraffin, or liquid polyethylene glycols. In addition, stabilizers can be added. All formulations for oral administration should be in dosages suitable for such administration.

For buccal administration, the pharmaceutical compositions can take the form of, e.g., tablets or lozenges formulated in a conventional manner.

For administration by inhalation, the targeting complex for use according to the present invention is conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit can be determined by providing a valve to deliver a metered amount. Capsules and cartridges of, e.g., gelatin for use in an inhaler or insufflator can be formulated containing a powder mix of the targeting complex and a suitable powder base such as lactose or starch.

The compositions and coated cells of the present invention can also be formulated in rectal compositions such as suppositories or retention enemas, e.g., containing conventional suppository bases such as cocoa butter or other glycerides.

In addition to the formulations described previously, the targeting complex of the present invention can also be formulated as a depot preparation. Such long acting formulations can be administered by implantation (for example subcutaneously or intramuscularly) or by intramuscular injection. Depot injections can be administered at about 1 to about 6 months or longer intervals. Thus, for example, the compositions and coated cells can be formulated with suitable polymeric or hydrophobic materials (for example as an emulsion in an acceptable oil) or ion exchange resins, or as sparingly soluble derivatives, for example, as a sparingly soluble salt.

In transdermal administration, the compositions and coated cells of the present invention, for example, can be applied to a plaster, or can be applied by transdermal, therapeutic systems that are consequently supplied to the organism.

Pharmaceutical compositions of the targeting complex also can include suitable solid or gel phase carriers or excipients. Examples of such carriers or excipients include but are not limited to calcium carbonate, calcium phosphate, various sugars, starches, cellulose derivatives, gelatin, and polymers such as, e.g., polyethylene glycols.

The compositions and coated cells of the present invention can also be administered in combination with other active ingredients, such as, for example, adjuvants, protease inhibitors, or other compatible drugs or compounds where such combination is seen to be desirable or advantageous in achieving the desired effects of the methods described herein.

In some embodiments, the disintegrant component comprises one or more of croscarmellose sodium, carmellose calcium, crospovidone, alginic acid, sodium alginate, potassium alginate, calcium alginate, an ion exchange resin, an effervescent system based on food acids and an alkaline carbonate component, clay, talc, starch, pregelatinized starch, sodium starch glycolate, cellulose floc, carboxymethylcellulose, hydroxypropylcellulose, calcium silicate, a metal carbonate, sodium bicarbonate, calcium citrate, or calcium phosphate.

In some embodiments, the diluent component may include one or more of mannitol, lactose, sucrose, maltodextrin, sorbitol, xylitol, powdered cellulose, microcrystalline cellulose, carboxymethylcellulose, carboxyethylcellulose, methylcellulose, ethylcellulose, hydroxyethylcellulose, methylhydroxyethylcellulose, starch, sodium starch glycolate, pregelatinized starch, a calcium phosphate, a metal carbonate, a metal oxide, or a metal aluminosilicate.

In some embodiments, the optional lubricant component, when present, comprises one or more of stearic acid, metallic stearate, sodium stearyl fumarate, fatty acid, fatty alcohol, fatty acid ester, glyceryl behenate, mineral oil, vegetable oil, paraffin, leucine, silica, silicic acid, talc, propylene glycol fatty acid ester, polyethoxylated castor oil, polyethylene glycol, polypropylene glycol, polyalkylene glycol, polyoxyethylene-glycerol fatty ester, polyoxyethylene fatty alcohol ether, polyethoxylated sterol, polyethoxylated castor oil, polyethoxylated vegetable oil, or sodium chloride.

Other embodiments are directed to a method of treating a cardiovascular disease in a subject in need thereof including the steps administering to the subject a pharmaceutical composition including a cell coated with a plurality of targeting complexes including a homing molecule, a lipid moiety, and a spacer covalently linking the homing molecule to the lipid moiety. As discussed above, the homing molecule may be presented on the outer surface of the cell and the lipid moiety may be non-covalently attached to the therapeutic cell and anchor the homing molecule to the cell. In some embodiments, a single administration of such a pharmaceutical composition may be sufficient to allow treatment. In other embodiments, the pharmaceutical composition may be administered two or more times through the course of treatment. For example, in some embodiments, administering may include administering the pharmaceutical composition once per day for 1 week, 2 weeks, 3 weeks, or a month or more, and in other embodiments, administering the pharmaceutical composition may include once per week administrations for one or more month.

The targeting technology of embodiments of the invention finds applicability for therapeutics in several clinical fields, such as, for example, cardiac ischemia or myocardial infarction (MI). The homing molecules, targeting complex and methods of embodiments of the invention can be useful for treating any of a variety of cardiopathies and cardiovascular diseases. Such cardiopathies and cardiovascular diseases include, but are not limited to, coronary artery disease (CAD); atherosclerosis; thrombosis; restenosis; vasculitis including autoimmune and viral vasculitis such as polyarteritis nodosa, Churg-Strass syndrome, Takayasu's arteritis, Kawasaki Disease and Rickettsial vasculitis; atherosclerotic aneurisms; myocardial hypertrophy; congenital heart diseases (CHD); ischemic heart disease and anginas; acquired valvular/endocardial diseases; primary myocardial diseases including myocarditis; arrhythmias; and transplant rejection. Cardiopathies and cardiovascular diseases to be treated according to a method of the invention further include, but are not limited to, metabolic myocardial diseases and myocardiomyopathies such as congestive, hypertrophic and restrictive cardiomyopathies, and heart transplants. A targeting complex of one embodiment of the invention will concentrate in the heart blood vessels and can further accumulate in the myocardium. Thus, the targeting complex, coated cell and methods of the invention are useful for treating these and other disorders of heart blood vessels or myocardium.

This invention and embodiments illustrating the method and materials used may be further understood by reference to the following non-limiting examples.

Example 1

Four synthesized peptides (PA-CRPPR, PA-CRKDKC, PA-KSTRKS and PA-SK(Biotin)NSCARSKNKDC) were coated onto human Mesenchymal Stem Cells (huMSCs) and the coated cells were systemically infused in a mouse myocardial infarction (MI) reperfusion model to specific targets within ischemic tissues.

On the practical side, the delivery of the cells via systemic circulation meant that adequate circulation to the infarcted heart tissue was necessary to provide the coated cells access via the cardiac circulation. From a clinical perspective, the patient population would likely have received standard of care within hours of presentation to a hospital (i.e., angioplasty and stenting), thereby establishing reperfusion of the tissue in advance of administration of cellular therapeutics.

Candidates for peptide-coated cell homing study were chosen based phage screening experiments and in vivo affinity studies to identify peptides demonstrated to home to tissues of choice. Development of appropriate lipidation process, cell membrane incorporation and efficacy of cell coating with the peptide were assessed. The lipidated peptides (or the coated cells) were labeled for flow cytometry evaluation and histological identification. Finally, after the labeled, peptide-coated cells were systemically infused in the mouse MI reperfusion model, the cells were located in the target and other tissues.

Example 1A

A limited phage screen of 12 phage was performed in a study against mice with myocardial infarction (MI) lasting 1, 3 and 7 days. This panel of phage was selected to include phage with a greater potential for injured tissue, a positive non-specific control and a negative control phage. The peptides expressed, and the affinities of these phage are shown in FIG. 24. All publications and references cited in FIG. 24 are incorporated by reference to the extent such incorporation is not contrary to the invention described therein. Nothing herein is to be construed as an admission that the invention is not entitled to antedate such disclosure by virtue of prior invention.

Amplified phage were mixed in a 1:1 ratio and 200 µl injected at $1\times10^9$ pfu/ml into animals 1, 3 and 7 days after myocardial ischemia was produced. Phage were allowed to circulate for 10 minutes before the animal was perfused through the left ventricle with warmed DMEM/BSA (1%, ~10 ml) with the right ventricle cut. Tissues (heart, lung, liver, spleen, kidney) were then harvested and stored on ice in 1 ml of DMEM/BSA (1%) before homogenization (Omni International TH homogenizer). Four washes were performed using PBS/BSA (1%) with centrifugation at 2800 RCF (5 min, 4° C.) and resuspension in PBS/BSA (1%). After the final wash, homogenates were weighed then lysed with 100 µl Triton-X-100 (1% in PBS) on ice for 15 minutes; 900 ul of BLT5403 (OD 600) was then added and incubated for 10 minutes (r.t.). This solution was then serially diluted in LB+CarbenicilHn and 240 ul aliquots taken into 1.2 ml BLT5403 and 600 µl plated on 10 cm agar plates with 4 ml top agar. Following overnight incubation, plaques were counted and the pfu/g tissue homogenate was calculated. Plaques were picked into 30 µl of PBS, 1 µl of this solution was transferred into 14 µl PCR mix (GoTaq Green Master Mix 7.5 µl, 1.5 µl 5 µM T7down (AAC CCC TCA AGA CCC GTT TA (SEQ ID NO: 13)), 1.5 µl 5 µM T7 Superup (AGC GGA CCA GAT TAT CGC TA (SEQ ID NO: 24)), 3.5 µl of DNAse free water). This mix was then subjected to polymerase chain reaction (PCR)

(1 cycle of 5 min 94° C.; 35 cycles of 94° C. 30 s, 50° C. 30 s, 72° C. 1 min; 1 cycle 72° C. 1 min; hold at 4° C.). The PCR samples then underwent cleanup and sequencing.

Fluorescently labeled CRPPR (SEQ ID NO: 1) was also studied for uptake and localization in ischemic hearts (30 minutes, 6 hour and 24 hour ischemia). This fluorescently labeled peptide was injected through the subclavian vein and allowed to circulate for two hours before sacrifice. Tissues (heart, lung, liver, spleen and kidney) were harvested, placed in TISSUE-TEK® molds and frozen in OCT cryomounting medium. The tissues were stored on dry ice until being placed at −80° C. and 8-10 μn sections were made.

RESULTS: Phage screening of a panel of peptides attached to phage in myocardial infarcted mice demonstrated some preferential localization of CRPPR (SEQ ID NO: 1), CARSKNKDC (SEQ ID NO: 5), CRKDKC (SEQ ID NO: 6), CREKA (SEQ ID NO: 8) peptides in the heart. A mutated phage, KSTRKS (SEQ ID NO: 14). surfaced in the first screen and was carried into the in vivo reperfusion model. Based on these data and the affinities of the peptides published in the literature, these four peptides were chosen as the candidates to be evaluated in the in vivo MI reperfusion model. Although CREKA (SEQ ID NO: 8) produced an encouraging display by phage screening, CREKA (SEQ ID NO: 8) was not able to be synthesized and purified with the necessary PA for cell coating and had to be excluded from the later studies.

Figure 4:
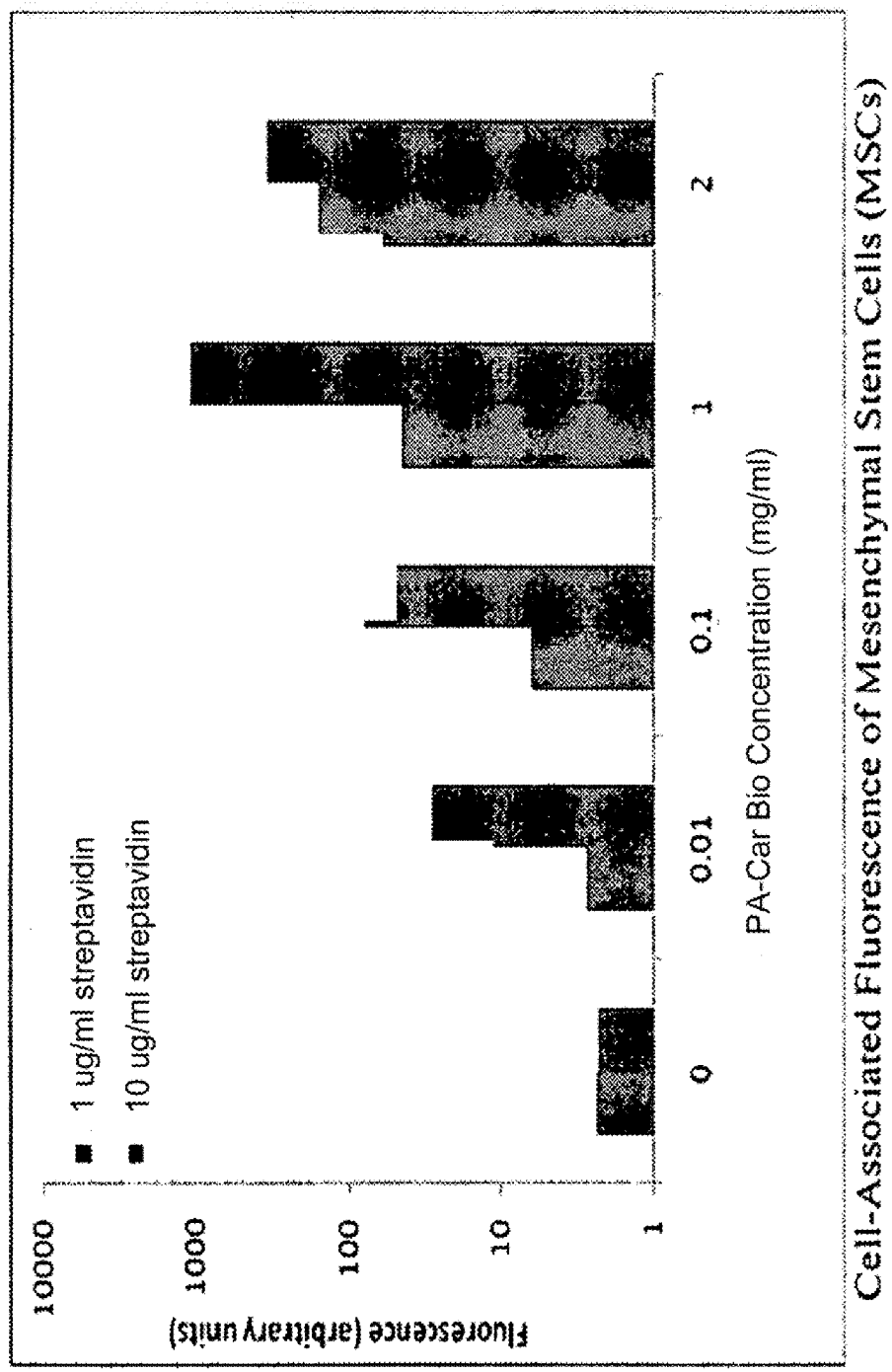
FIG. 4 illustrates cell-associated fluorescence of mesenchymal stem cells. This semi-log plot shows increasing cell-associated fluorescence with increasing PA-BioCAR (SEQ ID NO: 28) concentration and demonstrates saturation of the streptavidin-PE.
Figure 5:
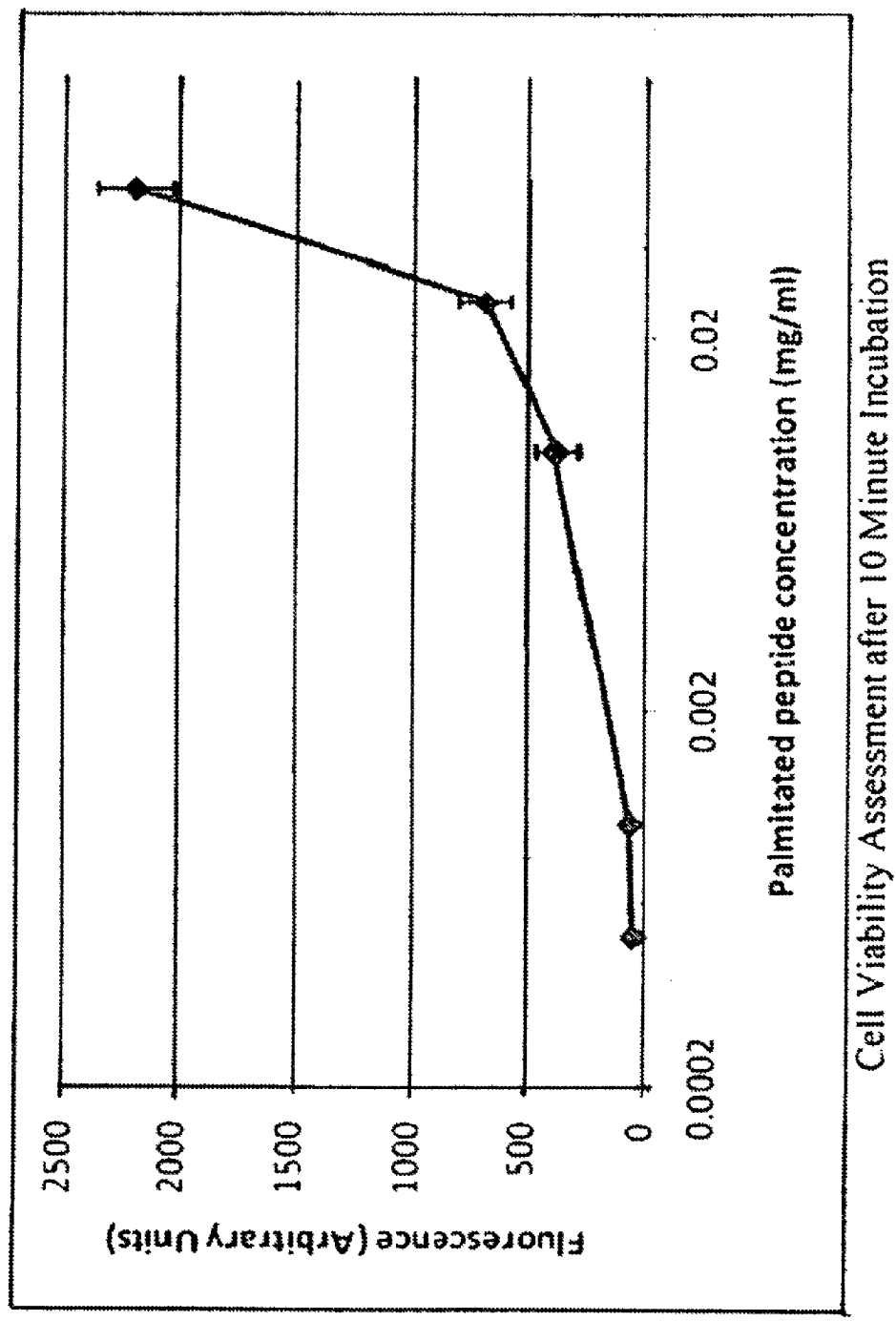
FIG. 5 is a graph showing increasing cell-associated fluorescence with increasing peptide concentration.
Figure 6:
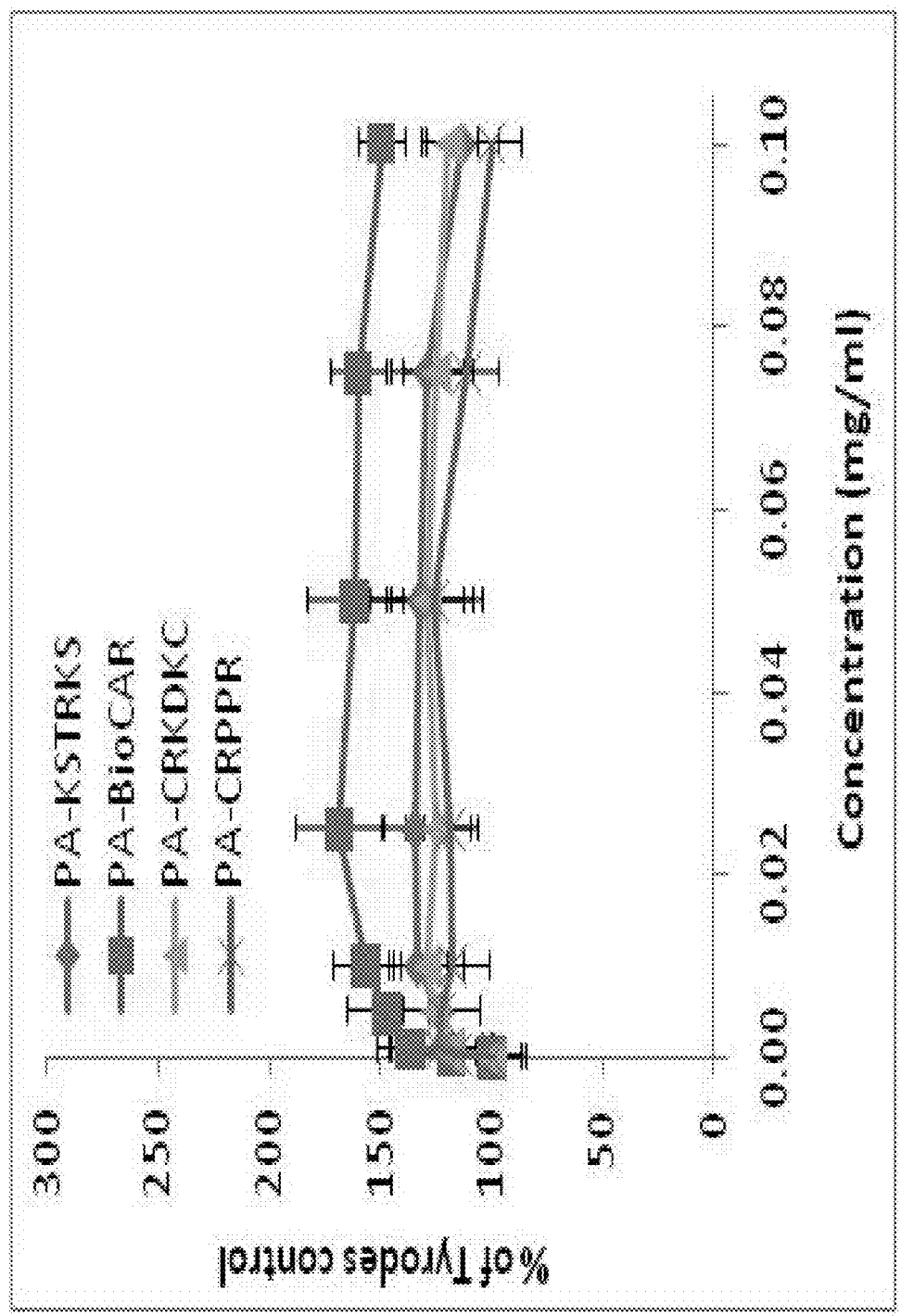
FIG. 6 is cell viability assessment after 10 minute incubation. The MTT assay showed increased mitochondrial activity of the cells after incubation with PA-peptides. No decrease was seen after 10 minute incubation (2 experiments with 6 replicates).
Figure 7:
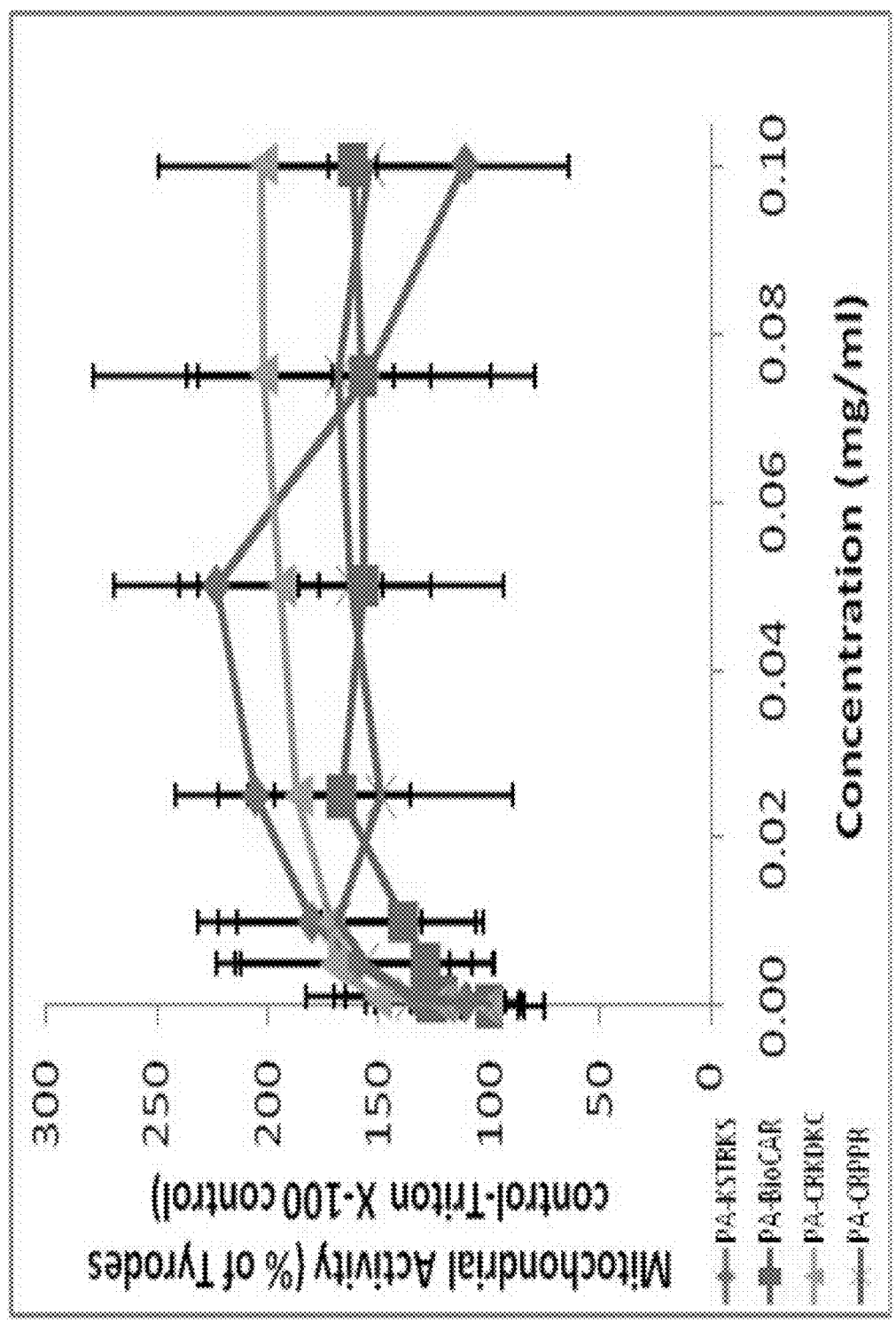
FIG. 7 is a cell viability assessment after 10 minute incubation with overnight stabilization. The MTT assay showed increased mitochondrial activity of the cells after incubation with PA-peptides. No decrease was seen after 10 minute incubation after cells were then allowed to recover overnight (2 experiments with 6 replicates).
Figure 8:
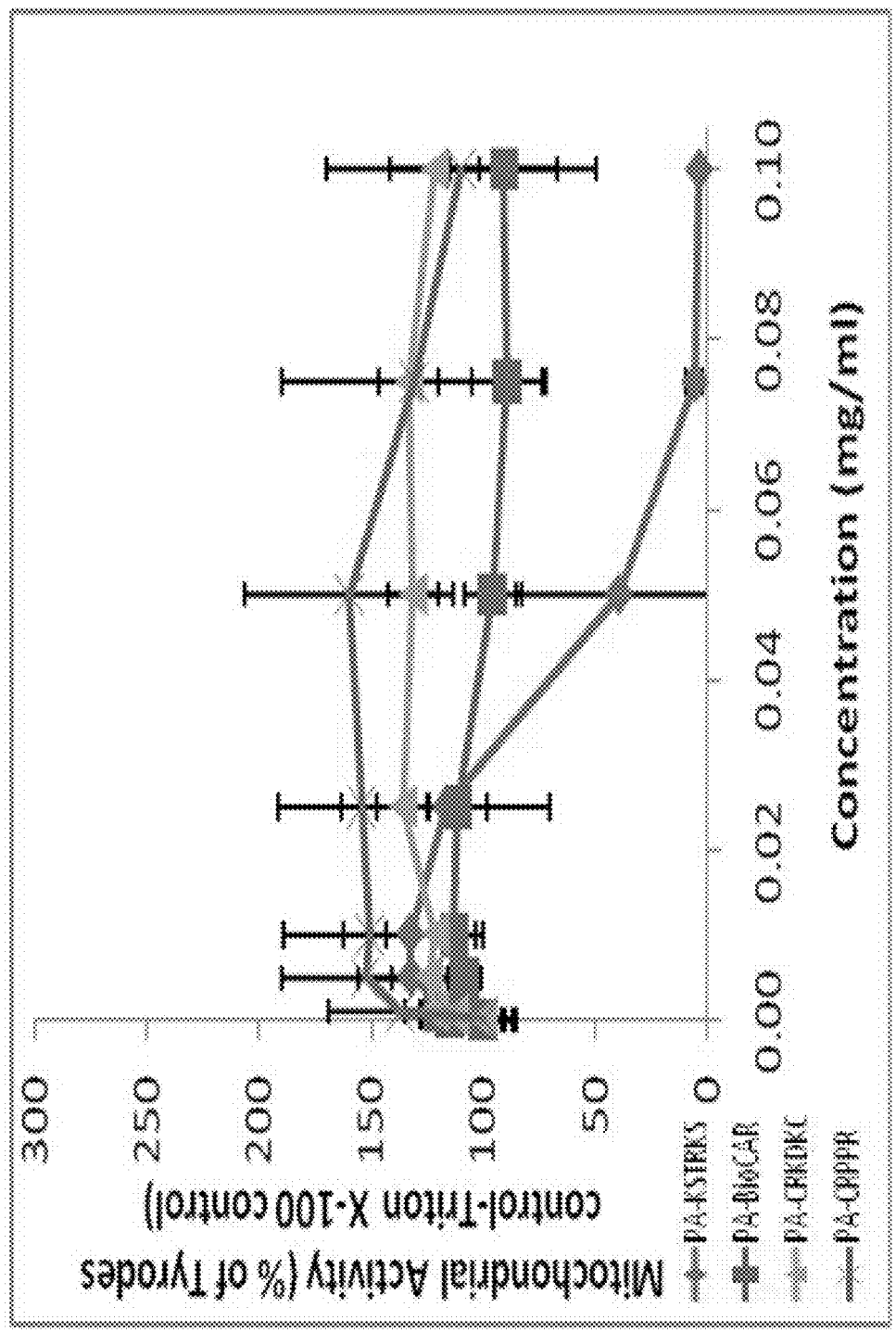
FIG. 8 illustrates the cell viability assessment after extended (1 hour) incubation. The MTT assay showed increased mitochondrial activity of the cells after incubation with all PA-peptides except PA-KSTRKS (SEQ ID NO: 25). PA-KSTRKS caused a decrease in mitochondrial activity at concentrations≥50 pg/ml (two experiments with six replicates).

Data on peptide concentration and association time for optimal coating method was produced using CARSKNKDC (SEQ ID NO: 5) with Biotin incorporated (BioCAR) to allow for Streptavidin-PE labeling, which could be detected via FLOW cytometric analysis (FIGS. 4, 5 and 9-11). Further viability experiments for all the peptides were conducted using the MTT assay for cell mitochondrial activity (FIGS. 6-8). In order to maximize labeling efficiency while minimizing detrimental effects to cell viability, final coating concentration determined for use in the in vivo experiments was set at 50 μg/ml PA-Peptide with a 10 minute incubation in DMEM.

Phage localization in the heart was relatively low, but plaque assessment revealed that CRPPR (SEQ ID NO: 1), CREKA (SEQ ID NO: 8) and CARSKNKDC (SEQ ID NO: 5) displayed some preferential localization in the heart. There was some preference for the earlier time point after infarct with CRPPR, and for the three day time point with CREKA. Three mutated phage showed up in the first screen and one, KSTRKS (SEQ ID NO: 14), was repeated in the second, as shown in Table 2.

Figure 2:
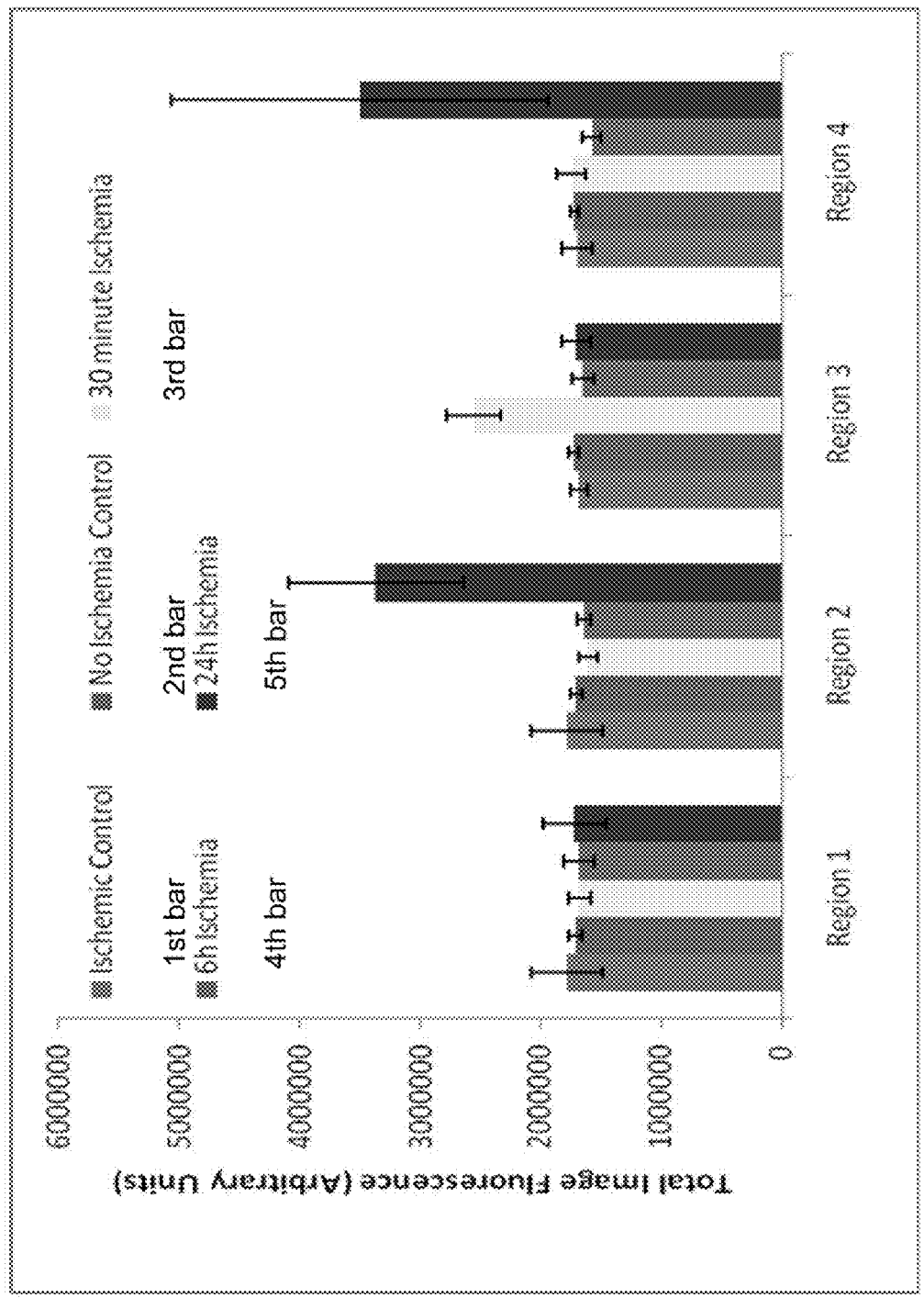
FIG. 2 is a semi-quantitative assessment of fluorescent peptide localization in heart tissue. Sections of heart tissue through different regions of the heart were imaged using a fluorescent microscope and CCD camera. The images were then assessed for total fluorescence using ImageJ (Image Processing and Analysis in Java).
Figure 3:
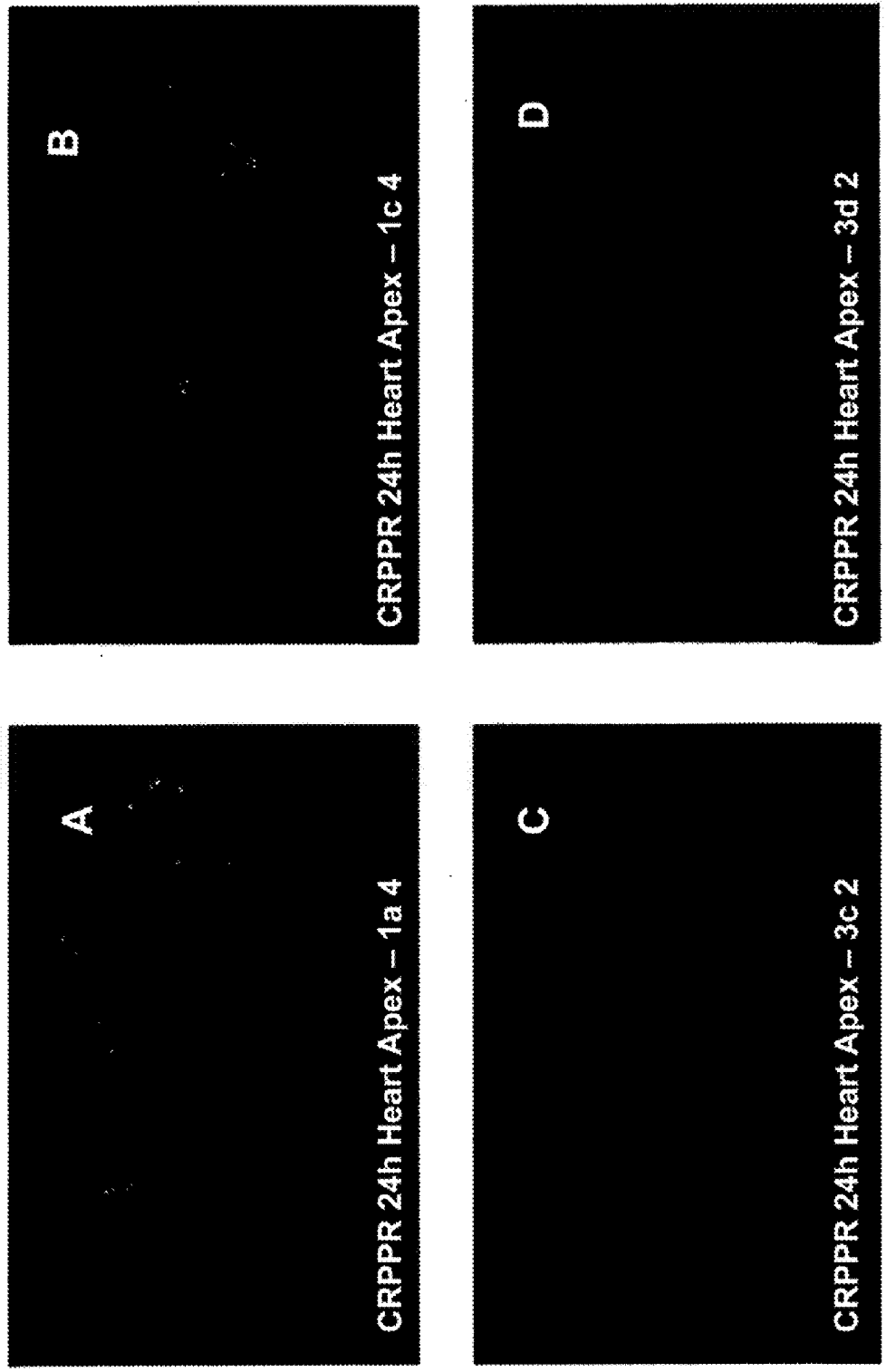
FIG. 3 contains fluorescent microscopy images of heart tissue from two different sampling regions of the 24 hour ischemic animal that show localization of CRPPR (SEQ ID NO: 1) (where A and C are from the same animal and B and D are from the same animal), but at different intensity levels (presuming different levels of targeting) in the two different regions (4 (A and B) and 2 (C and D)).

As shown in FIGS. 2 and 3, fluorescent CRPPR (SEQ ID NO: 1) was seen to localize in heart tissue. This localization was region-specific and was most pronounced after 24 hour ischemia. Sections of heart tissue through different regions of the heart were imaged using a fluorescent microscope and CCD camera. The images were then assessed for total fluorescence using ImageJ (Image Processing and Analysis in Java) (see FIG. 2).

Example 1B

Cell coating with lipidated peptides was assessed using PA-BioCAR coated onto human mesenchymal stem cells (MSCs). MSCs were grown in Dulbecco's Modified Eagle's Medium (DMEM) and fetal bovine serum (FBS) (10%) supplemented with fibroblast growth factor-2 (FGF-2) (5 ng/ml) for 1 week. They were then trypsinized, washed with DMEM, aliquoted at 1 million cells/vial and resuspended in Tyrodes' balanced salt solution. DMEM was later used throughout the coating procedure. Concentrations of PA-BioCAR between 0 and 2 mg/ml were applied to the cells and incubated (37° C.) with shaking for 10 minutes. Cell solutions were centrifuged (200 RCF, 5 min, r.t.), washed twice with cold Tyrodes solution, then incubated for 20 minutes with 20 μg/ml streptavidin-PE (S866 Invitrogen), washed with Tyrodes solution, fixed with formalin, and then assessed using flow cytometry and epifluorescent microscopy.

In association and dissociation experiments, the cells were coated with PA-BioCAR as above, washed and stored in DMEM at 4° C. or 37° C. for up to 3½ h, at each time point an aliquot was centrifuged (200 RCF, 5 min, 4° C.) and fixed with formalin. At the end of the experiment, all samples were labeled with streptavidin-PE 0.1 mg/ml for 20 min, washed and resuspended in phosphate buffered saline (PBS) for flow cytometry.

RESULTS: The semi-log plot of FIG. 4 shows increasing cell-associated fluorescence with increasing PA-BioCAR concentration. The semi-log plot shown in FIG. 4 also demonstrates saturation of streptavidin-PE. The peptide labeled the cells efficiently, as shown in FIGS. 4 and 5, but the cells looked perturbed at higher concentrations. Washing and gentle handling of the cells improved coating, and cell coating was optimized with a 10 minute incubation (50 ug/ml PA-Peptide) in DMEM. FIG. 5 is a graph showing increasing cell-associated fluorescence with increasing peptide concentration. FIG. 6 is cell viability assessment after 10 minute incubation.

Figure 9:
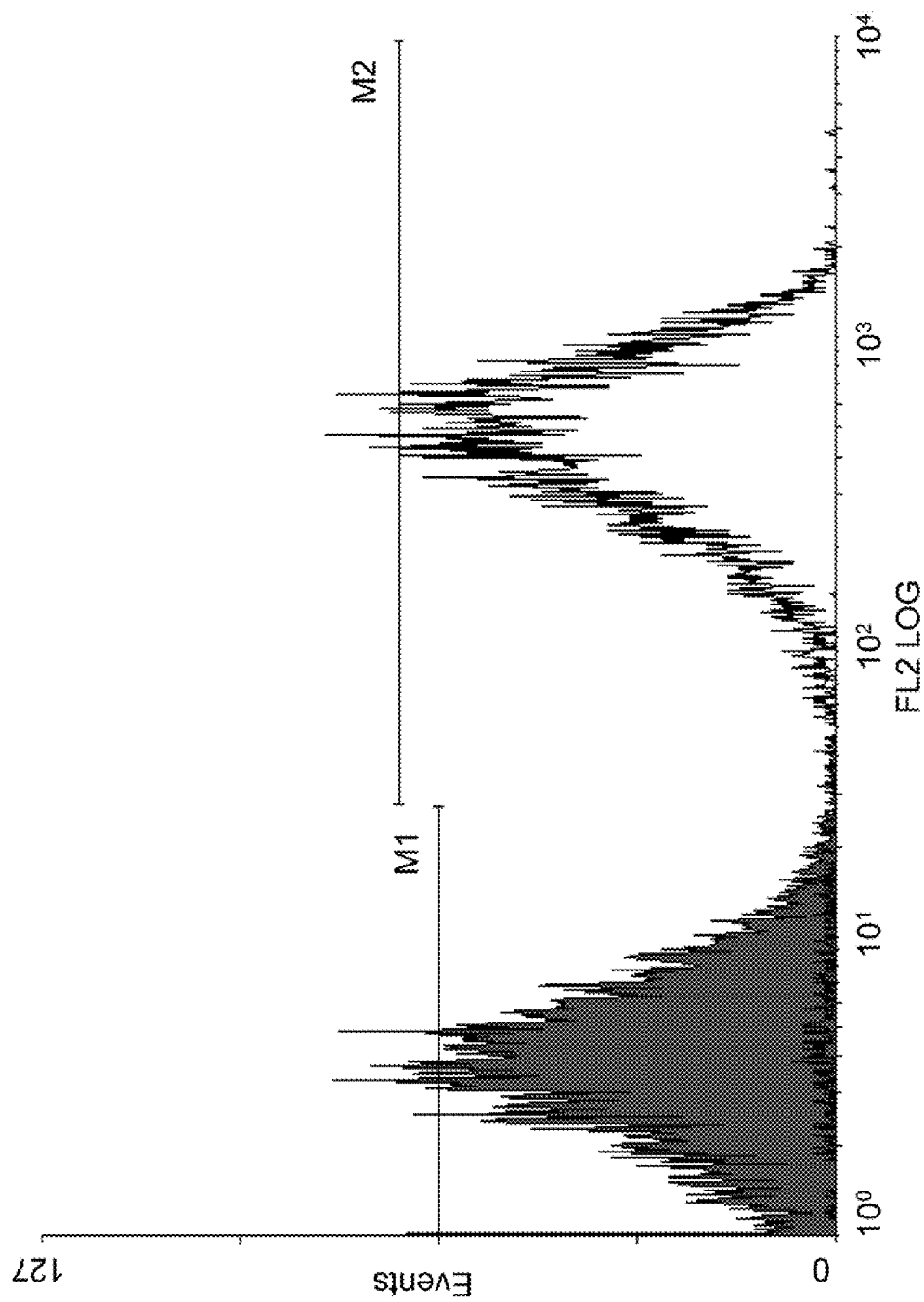
FIG. 9 illustrates the flow cytometry positive and negative cell populations. The negative cell population was set as M1 (filled) and the positive cell population was set as M2 (open histogram).
Figure 10:
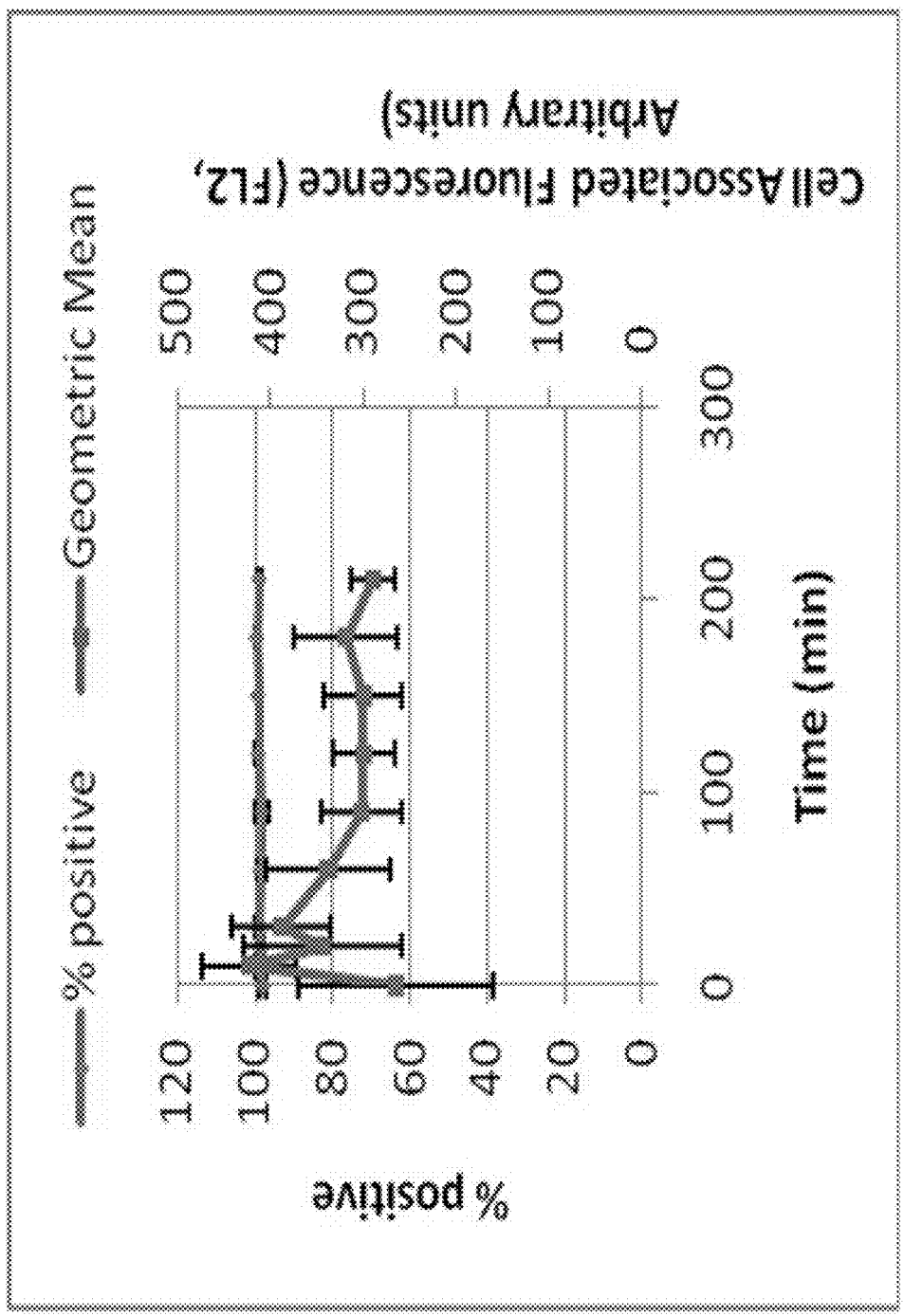
FIG. 10 illustrates 4° C. dissociation of PA-BioCAR (SEQ ID NO: 28) from cells. The percent positive cells are shown on the left scale and the cell-associated fluorescence is shown on the right scale (n=3, >5000 events±S.D.).
Figure 11:
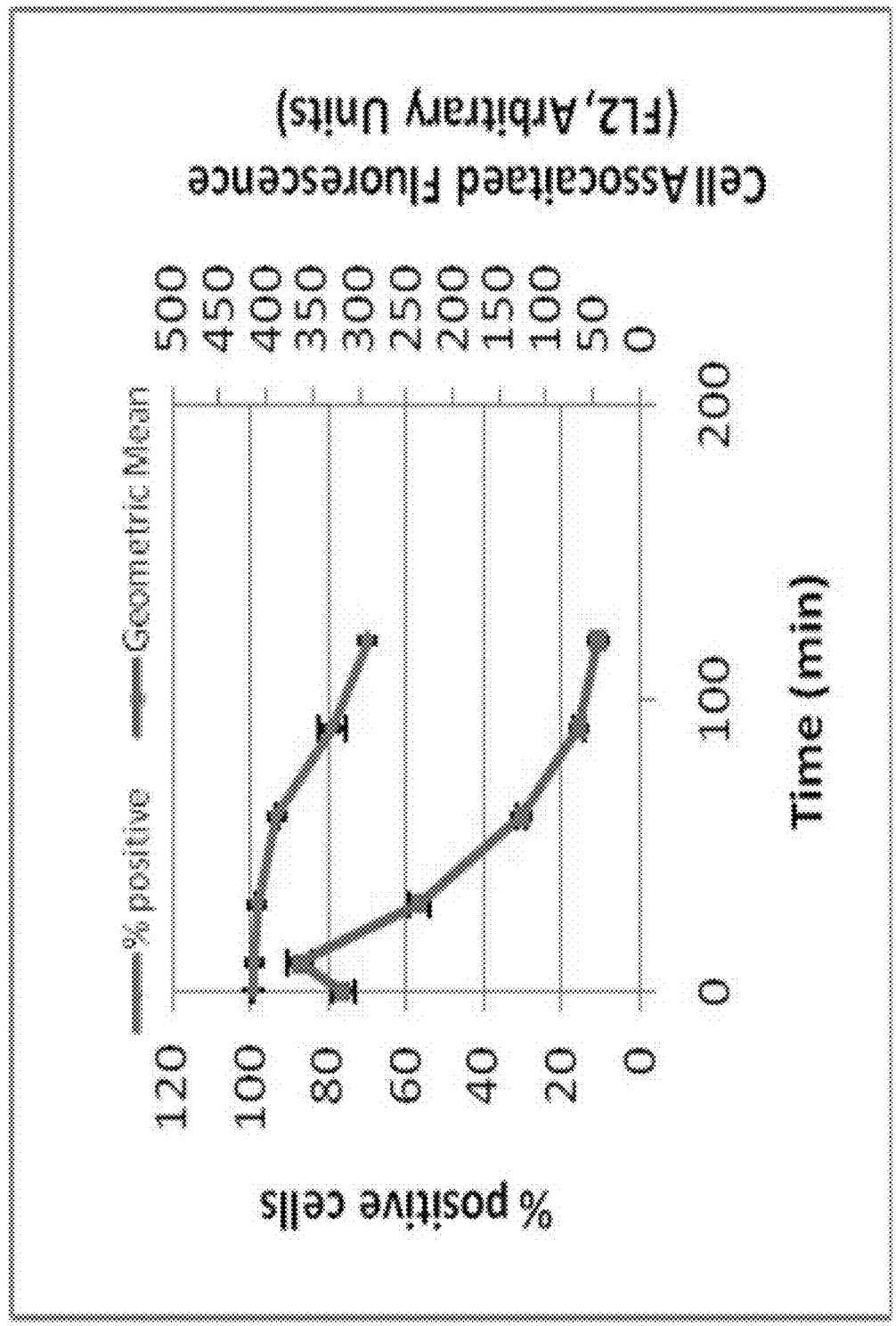
FIG. 11 illustrates 37° C. dissociation of PA-BioCAR (SEQ ID NO: 28) from cells. The percent positive cells are shown on the left scale and the cell-associated fluorescence is shown on the right scale (0-90 min n=3, 120 min n=1, >5000 events±S.D.).

The dissociation of PA-BioCAR, from hMSCs was determined at 4° C. and 37° C., as shown in FIGS. 9 to 11. In FIG. 9, a large shift in cell-associated fluorescence is evident, and little decrease is seen in either the percentage positive cells or the cell-associated fluorescence at 4° C. (shown in FIG. 10). At 37° C., although there was little decrease in the percent positive cells, there was a time dependent decrease in cell-associated fluorescence, as illustrated in FIG. 11.

Example 1C

Four palmitated peptides (cell paints) were synthesized: PA-CRPPR, PA-CRKDKC, PA-KSTRKS and PA-SK(Biotin)NSCARSKNKDC (cyclized between the cysteines) (Biomatik USA LLC, Wilmington, Del.). See FIG. 13.

Human mesenchymal stem cells (MSCs) were seeded on 96-well plates ($5.8 \times 10^3$ cells/well; DMEM/FBS 10%) and allowed to grow/adhere for 2 days. Media was removed and PA-peptides were added (0-0.1 mg/ml) to the cells. Toxicity was assessed after 10 minute incubation and 1 hour incubation. Acute effects were assessed immediately following the 10 minute exposure, and longer-term effects were measured the next day after the 10 minute exposure and the 1 hour exposure. Toxicity was assessed using the MTT method. Briefly, 20 μl of MTT (5 mg/ml in PBS, sterile filtered, Corning 0.22 μm Polyethersulfone) was added to each well and the plate was then incubated for 4 hours at 37° C. Media containing MTT was then carefully removed and 100 μl of dimethyl sulfoxide (DMSO) was added to each well. Plates were incubated for a further 30 minutes at 37° C. to solubilize the purple formazan crystals, and absorbance was then measured using a plate reader (570 nm; Tekan Genios Pro).

RESULTS: The MTT assay showed increased mitochondrial activity of the cells after incubation with PA-peptides. No decrease was seen after 10 minute incubation (2 experiments with 6 replicates). FIG. 7 is a cell viability assessment after 10 minute incubation with overnight stabilization. The MTT assay showed increased mitochondrial activity of the cells after incubation with PA-peptides. No decrease was seen after 10 minute incubation after cells were then allowed to recover overnight (2 experiments with 6 replicates). FIG. 8 illustrates the cell viability assessment after extended (1 hour) incubation. The MTT assay showed increased mitochondrial activity of the cells after incubation with all PA-peptides except PA-KSTRKS. PA-KSTRKS caused a decrease in mitochondrial activity at concentrations≥50 ug/ml (2 experiments with 6 replicates).

Example 1D

For animal experiments, MSCs were first incubated with VYBRANT® green (CDFA SE; Invitrogen), washed with DMEM, then coated with 50 µg/ml PA-peptides for 10 minutes at 37° C. with shaking. Four palmitated peptides (cell paints) were synthesized: PA-CRPPR, PA-CRKDKC, PA-KSTRKS and PA-SK(Biotin)NSCARSKNKDC (cyclized between the cysteines) (PA-BioCAR) (Biomatik USA LLC, Wilmington, Del.). Following PA-Peptide coating, cells were washed with DMEM twice and resuspended to give $5 \times 10^6$ cells/ml. Animals were then injected through the left ventricle ($1 \times 10^6$ cells/ml) and cells were allowed to circulate for 1 hour before sacrifice.

C57BL6 mice were operated on with a sterile surgical technique. Mice were anaesthetized and intubated. A longitudinal incision was made in the thorax and the heart elevated. The left anterior descending artery was identified, and a ligature suture was placed around the artery and tightened down over a piece of polyethylene tubing placed above the artery, as shown in FIG. 1. After 30 minutes the ligation was released, the chest closed and the mouse was allowed to recover. The following day the mouse was again anaesthetized and intubated, the thoracotomy re-opened and cells administered through the left ventricle ($1 \times 10^6$ cells). Cells were allowed to circulate for 1 hour before blood was collected into EDTA tubes and the mouse sacrificed via exsanguination. Blood was collected just prior to exsanguination to provide samples for assay of Troponin I levels.

Upon excision, hearts were immersed immediately in phosphate buffered saline (10 mL), cross-sectioned sagitally through the infarct site at the level of the suture, and the pairs of rostral atrial and caudal apical sections were embedded in OCT cryomounting medium for immediate freezing (lung, liver, spleen and kidney tissue were also collected and frozen in OCT). Sections were cryosectioned 8 microns thick, mounted in sequence onto slides and viewed for the fluorescent label of the cells.

Histology sections of cardiac tissues were examined for VYBRANT® (CDFA SE; Invitrogen) green-labeled cells to determine the cells' propensity to target or home to distinct regions of the tissues, especially those associated with the infarcted region. Outcomes were evaluated via quantitative fluorescent microscopy of infarcted and non-infarcted tissues. Area in millimeters squared were calculated from representative cross-sections and numbers of cells were counted on a series of sections taken through the heart.

Sections of heart tissue were also analyzed using fluorescent microscopy. Five slides containing six sections per slide were analyzed. On each section a count of the number of cells was made. The count was then normalized against the area of the centre section on that slide.

Figure 12:
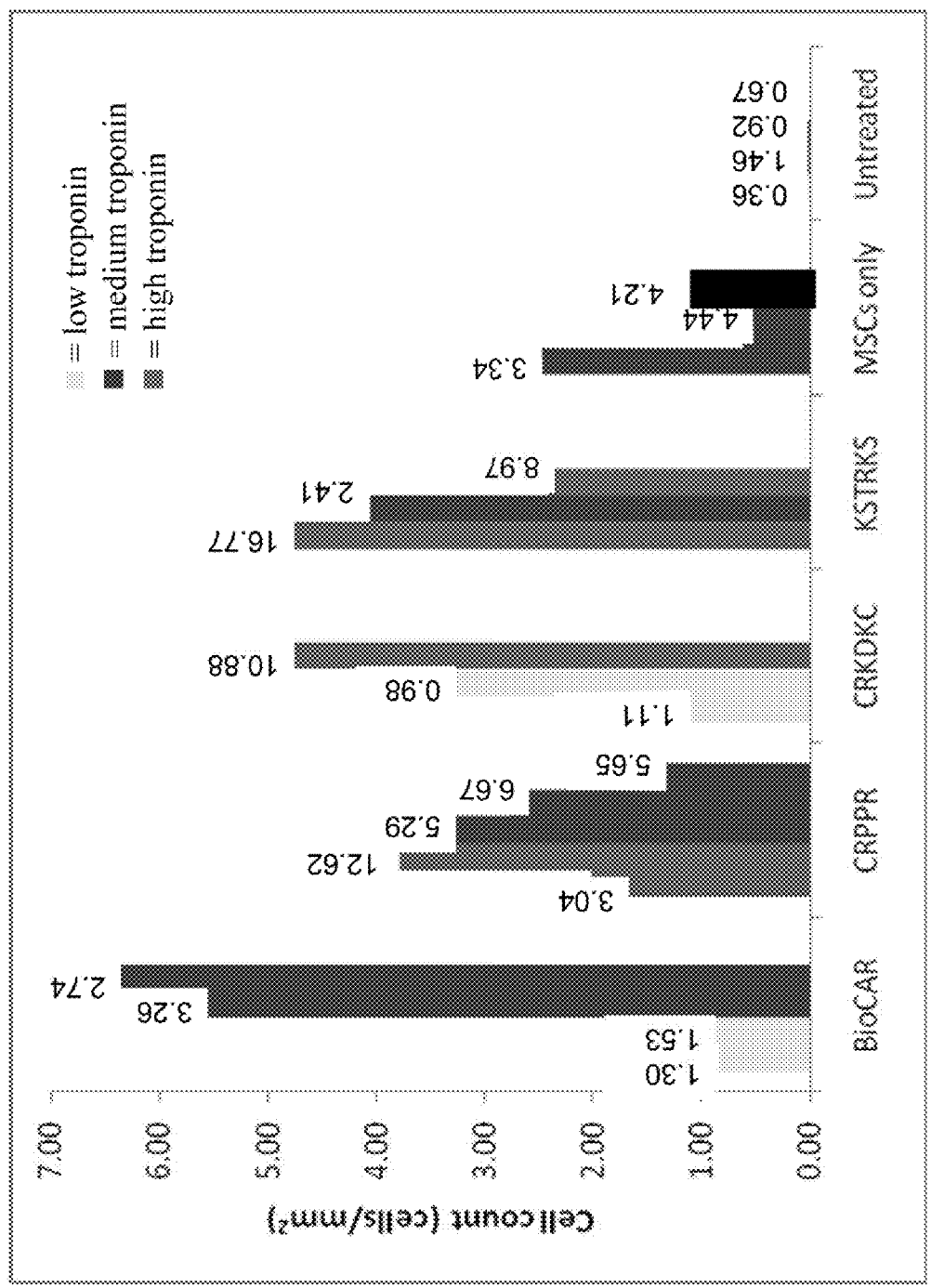
FIG. 12 illustrates an assessment of cell homing and heart damage in the mouse MI reperfusion model. Each bar represents the average cell count of an animal (30 sections); three to five mice were tested for each treatment cohort. The number above the bar is the ELISA assessment of plasma concentration of cardiac troponin I.
Figure 13A:
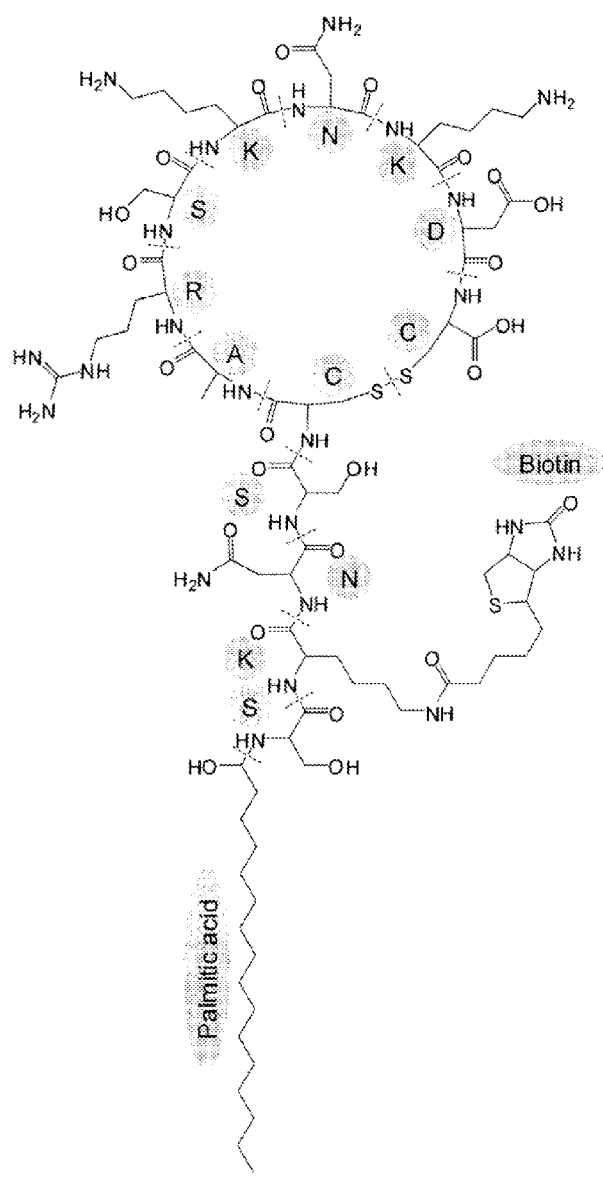
FIG. 13 illustrates the chemical structures of four palmitated-peptides: PA-BioCAR (SEQ ID NO: 28), PA-CRPPR (SEQ ID NO: 26), PA-CRKDKC (SEQ ID NO: 27) and PA-KSTRKS (SEQ ID NO: 25).
Figure 13B:
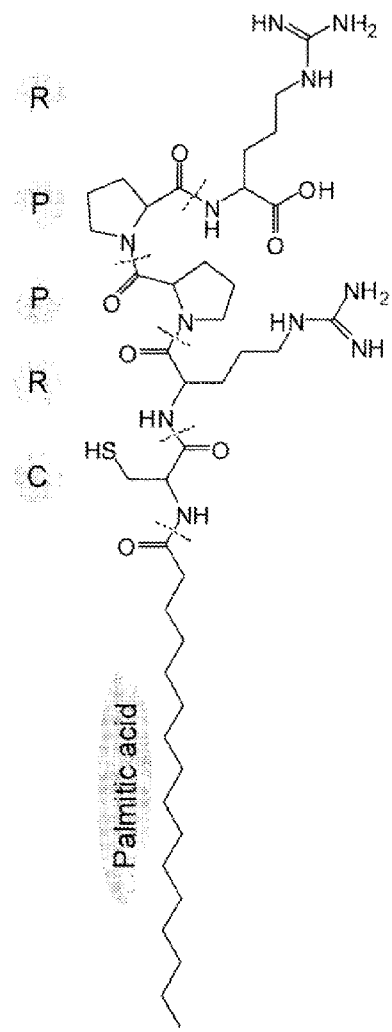
Figure 13C:
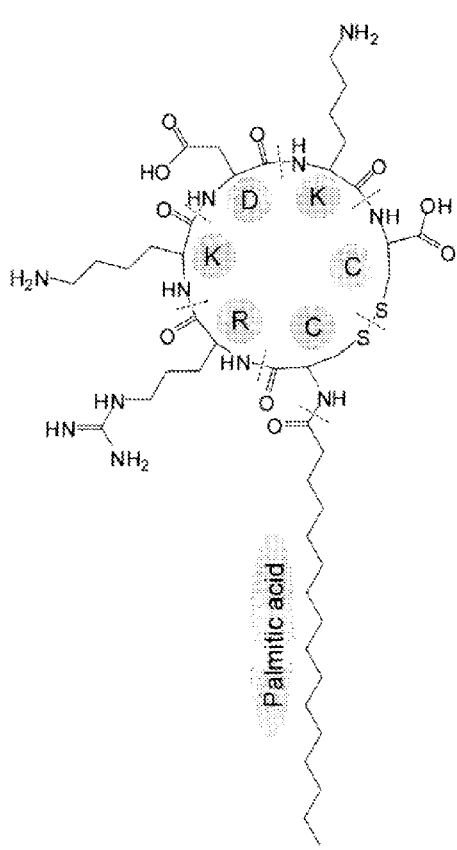
Figure 13D:
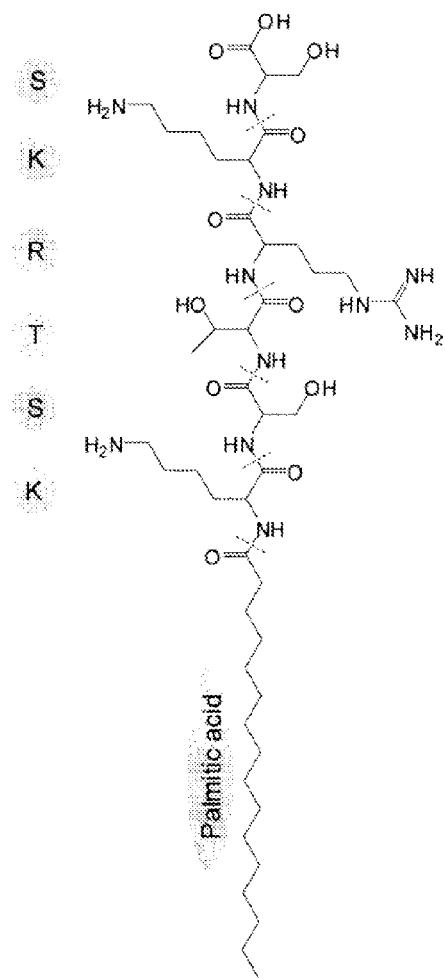
Figure 14:
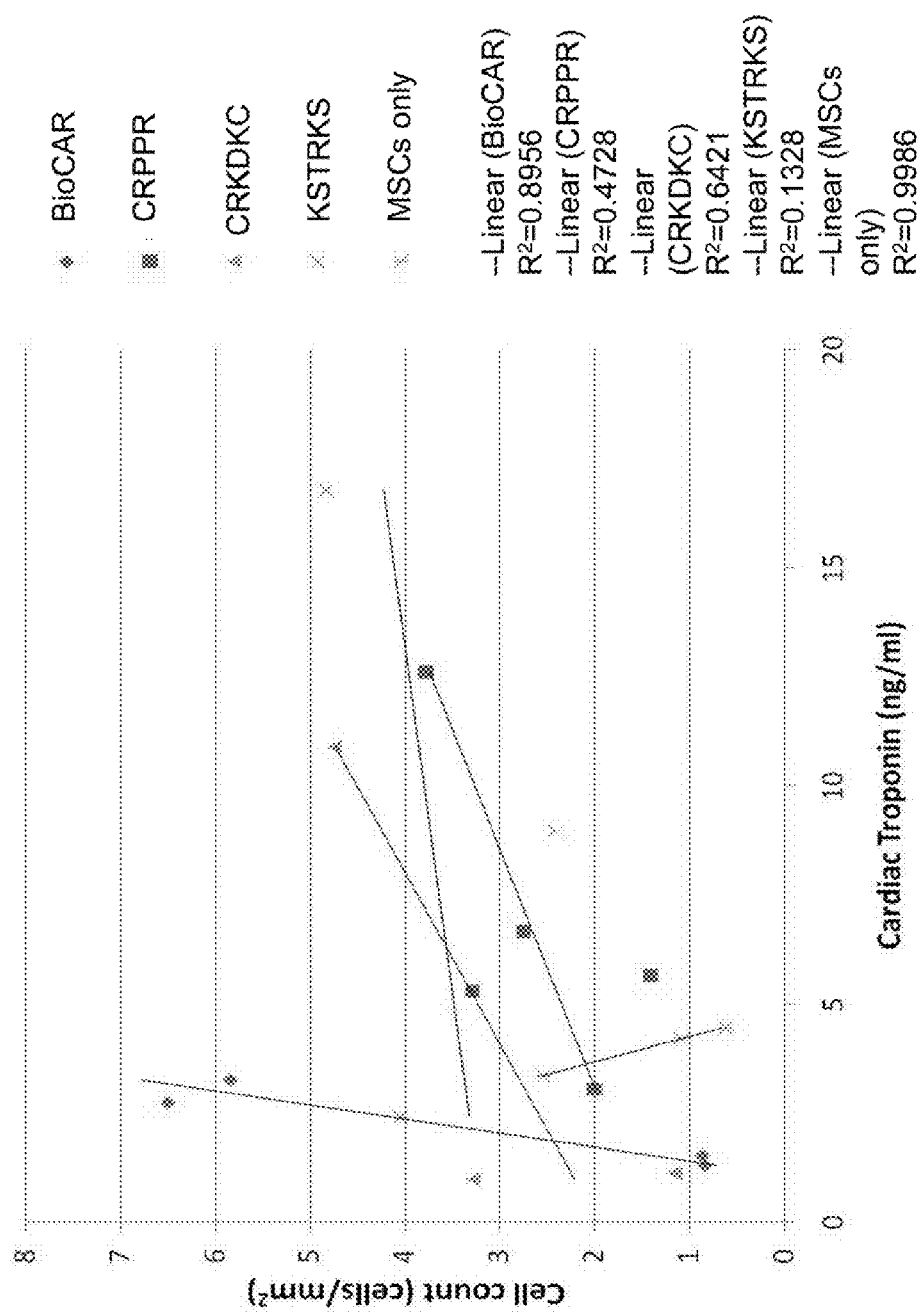
FIG. 14 illustrates the correlation between heart damage and cell targeting. The individual values of cardiac troponin and cell number gained for each animal are shown with lines fitted and their correlation coefficient noted below the line in the legend.

RESULTS: As with any animal model, the biological variability in this model system, due in part to variability of heart vascularization, translates to a high degree of variability in the size and severity of the ischemic region after ligation procedure. There was considerable variation in the extent of damage produced by the ischemia reperfusion injury as indicated by the serum troponin levels (FIGS. 12 and 14). There is a correlation between increase damage and increased cell numbers (FIG. 14); this is especially relevant in PA-BioCAR coated cells. Correlation data showed positive curves with all peptide targeted groups and a negative correlation with MSCs along (FIG. 14). When sections of the heart were compared, there was often a dramatic difference in the number of cells that had localized to the cardiac tissue when peptide coating had been applied (FIG. 2).

Indeed, cardiac spermatid nuclear transition protein-I (TNP I) levels provided an indication to what degree infarction varied from mouse to mouse. Even in the face of such variability and low "n" values, higher cell counts/mm$^2$ of cross-sectional tissue were observed in the majority of mice from all peptide-coated cell treated cohorts, as compared to the cell alone treatment group.

Figure 26:
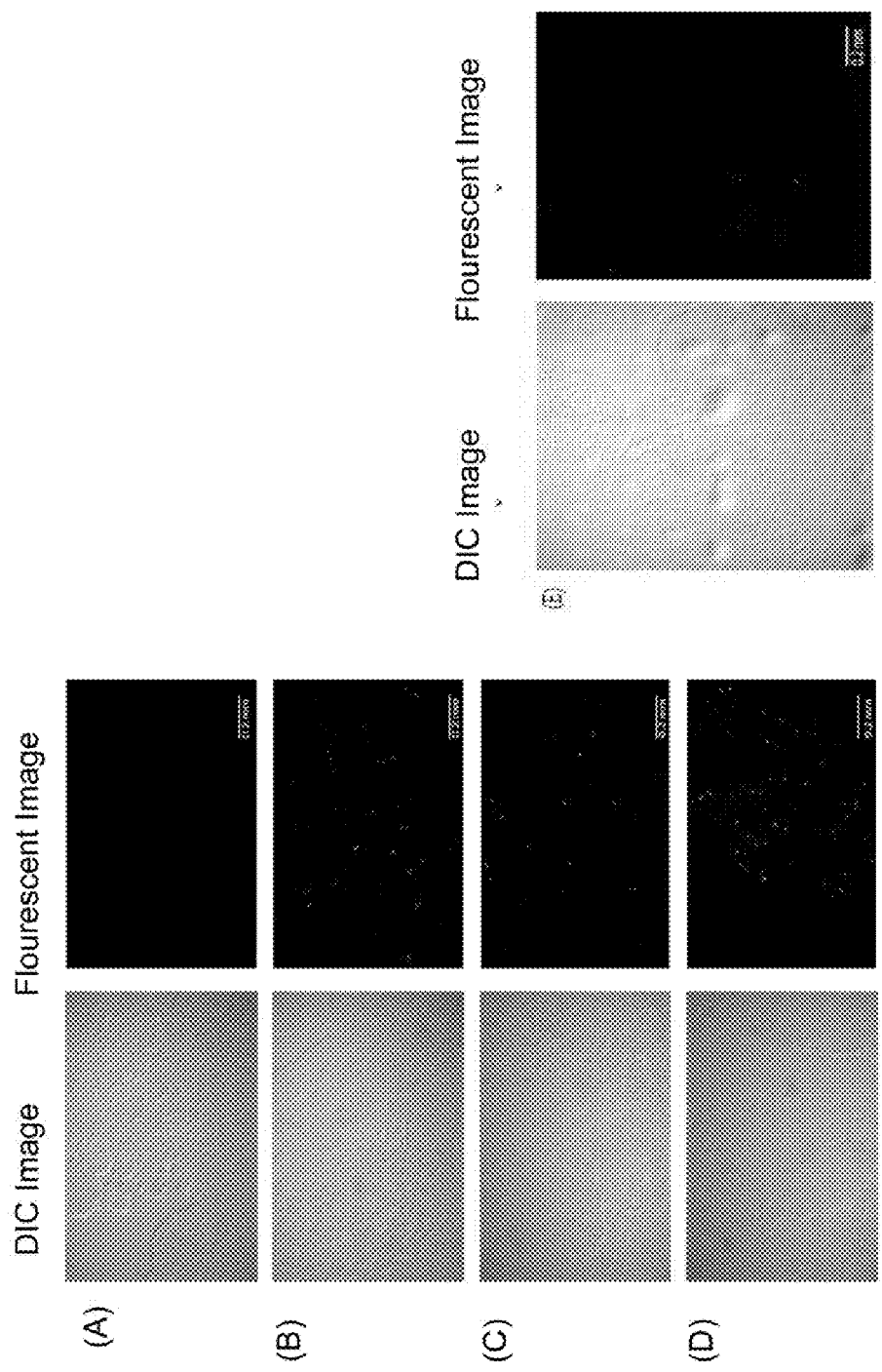
FIG. 26 illustrates representative examples of the localization of cells within heart tissue. 26A: Cells only, 26B: PA- BioCAR (SEQ ID NO: 28), 26C: PA-CRPPR (SEQ ID NO: 26), 26D: PA-CRKDKC (SEQ ID NO: 27), 26E: PA-KSTRKS (SEQ ID NO: 25).

In analysis of the targeted homing of MSCs to hearts after myocardial infarction, there was a large variability in the damage caused by the infarct, as shown in FIG. 11. It appears that in the PA-BioCAR coated cell group, this produced two distinct groups with more cells localizing in the heart after relatively larger damage. In terms of the distribution, the cells appeared to be distributed throughout the cardiac muscle in PA-BioCAR. In PA-CRPPR, there appears to be some localization with vasculature. With PA-CRKDKC papillary fibers have a higher concentration of cells than the cardiac muscle. PA-KSTRKS shows distributed cells with some localization in vessels. MSCs alone were distributed throughout the cardiac muscle. Such patterns are difficult to discern viewing fluorolabeled cells on a black background, even with reference back to phase contrast fields of view. These patterns will be further elucidated using histology probes or antibodies specific for certain aspects of the micro-anatomy of the tissues, such as the endothelium of vessel walls. The images in FIG. 26 give representative examples of the localization of cells within heart tissue. As shown in FIG. 12, when comparing the targeted cells to MSCs alone, all targeted groups show more cells homing to the heart.

Example 1E

An enzyme-linked immunosorbent assay (ELISA) (Life Diagnostics, Inc., Cat. No. 2010-1-HSP) of cardiac troponin I was made on the plasma collected from each mouse according to the manufacturer's method. Briefly, 60 µl of plasma sample was diluted with 180 µl plasma diluent. Standards and samples (100 µl) were added to coated wells containing 100 µl of cardiac troponin I horse radish peroxidase conjugate. These were mixed on an orbital shaker at room temperature for 1 hour. This solution was removed and the wells were washed thoroughly; 100 µl of tetramethylbenzidine reagent was then added to each well. This was incubated on the orbital shaker at room temperature for 20 minutes, then stop solution was added (100 µl) and the absorbance read at 450 nm (Tecan Genios Pro).

RESULTS: From the data shown in FIGS. 4-8 and based on an absence of trypan blue staining at 50 µg/ml concentrations of PA-peptides, 50 µg/ml was chosen as the optimal concentration to label cells. This was determined due to a high cell coating with minimal cell perturbation. After coating at this concentration, an appreciation of the duration of labeling was sought. In animal experiments, there is often a lag between labeling of the cells and administration to the animal. During this time the cells are kept on ice.

Coating is an efficient process that can be maintained on the cells by storage at 4° C. for up to 3½ hours. The paint is lost over time at 37° C., which may be desirable (long term labeling could be detrimental to the cell), but the dissociation profile may not yet be optimal. The kinetics of the cell localization, distribution, redistribution and paint loss are dynamics requiring further elucidation. However, FIG. 10 shows that 70% of the cells are still positive.

These examples were designed to provide a survey of several peptides for their affinity to cardiac tissues, refinement of peptide coating techniques including assessment of optimal coating concentrations and effects on cell viability, and in vivo experiment of coated cells as an initial screening of peptide-coated cells' distribution in the ischemic heart. The data presented demonstrates peptide-mediated targeting of cells to the heart. The homing peptide was able to efficiently intercalate into the cell membrane in a non-toxic manner. All synthesized peptide coatings were able to increase the efficiency of stem cell homing to infarcated hearts. In addition, the coating method has been shown to be well-tolerated by the cells through cell viability experiments.

Example 2

Four palmitated peptides were synthesized: SK(biotin) NSCARSKNDKC (PA-BioCAR), PA-KSTRKS, PA-CRPPR and PA-CRKDKC. In fluorescent peptide studies, PA-BioCAR homed to ischemic skeletal muscle tissue, PA-KSTRKS homed to ischemic skeletal muscle tissue, PA-CRPPR homed to cardiac tissue, and PA-CRKDKC homed to ischemic muscle tissue. Human mesenchymal stem cells (hMSCs) were transiently coated with the four palmitated peptides and fluorescently labeled with Vybrant dye. Cell coating with lipidated peptides was assessed using PA-BioCAR coated onto human mesenchymal stem cells (MSCs). MSCs were grown in DMEM/FBS (10%) supplemented with FGF (5 ng/ml), then trypsinized, washed with DMEM and aliquoted at 1 million cells/vial and resuspended in Tyrodes. Concentrations of PA-BioCAR between 0 and 2 mg/ml were applied to the cells and incubated with shaking for 10 minutes. Cell solutions were then centrifuged (200 RCF, 5 min, r.t.), washed twice with cold Tyrodes, then incubated for 20 min with 20 µg/ml streptavidin-PE (S866 Invitrogen), washed with Tyrodes, fixed with formalin, and then assessed using flow cytometry and epifluorescent microscopy.

For animal experiments, MSCs were first incubated with Vybrant green (CDFA SE; Invitrogen) washed with Tyrodes, then coated with 50 µg/ml PA-peptides for 10 min at 37° C. with shaking. Following coating, cells were washed with Tyrodes twice and resuspended to give $5 \times 10^6$ cells/ml. Ischemia was produced in the left hind-limb through ligation and severing of the femoral artery in mice. Three days post ischemia, mice were injected with 100 µg of peptide/mouse through the subclavian vein and cells allowed to circulate for two hours before sacrifice. Distribution of injected MSCs was monitored by whole-body ("Xenogen") fluoroscopy. Animals were sacrificed and tissues (heart, lung, liver, spleen, kidney, left calf muscle, left femur muscle, right calf muscle and right femur muscle) were harvested and fluorescence histology was done on tissue cryosections.

Figure 15:
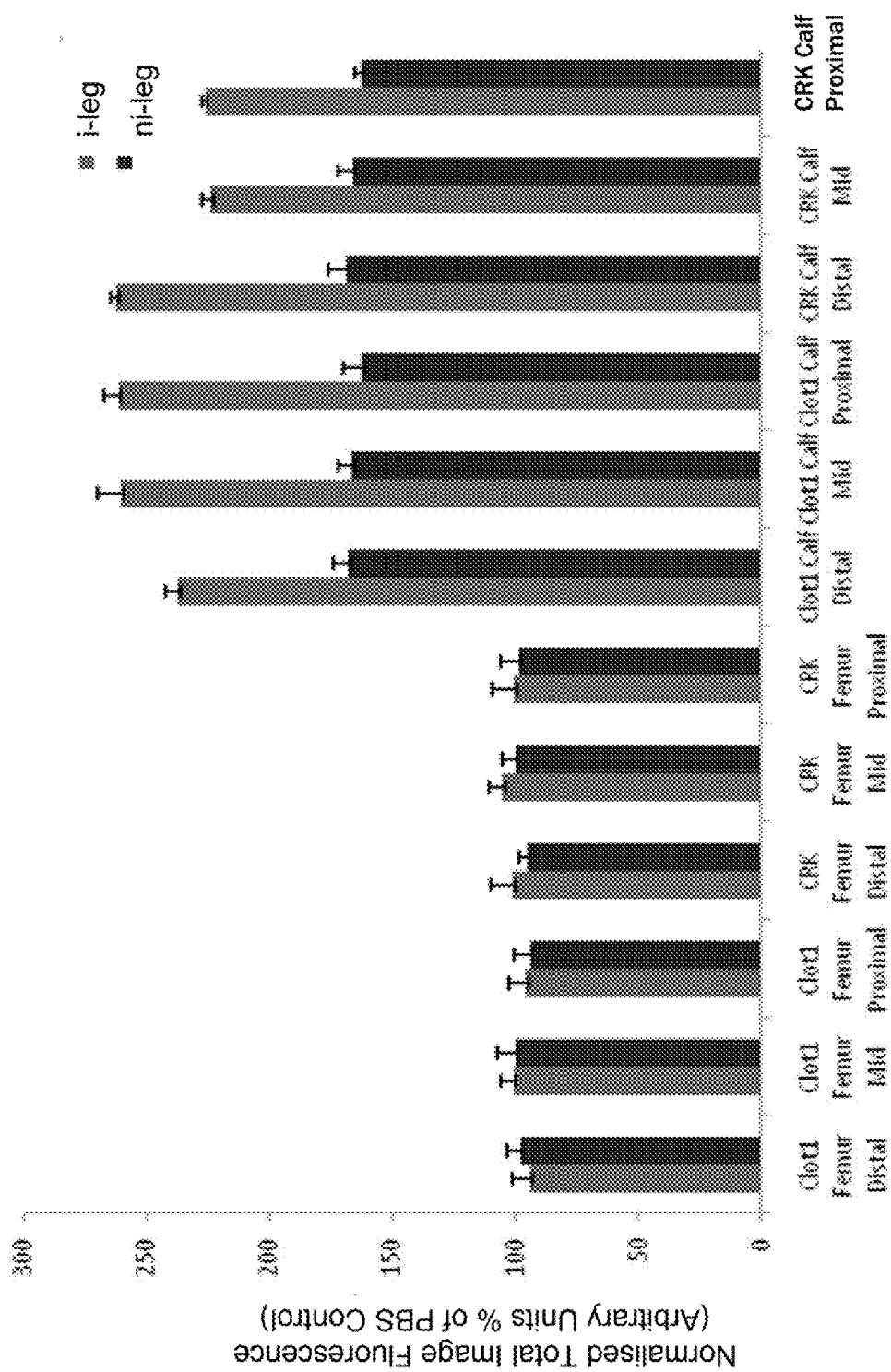
FIG. 15 illustrates the normalized average total image fluorescence of ≥9 slices taken from distal, mid and proximal locations of the femoral ("femur") or tibial ("calf") section of the tissue. N≥2 animals±SEM. CRKDKC ("CRK") (SEQ ID NO: 6); CGLIIQKNEC ("CLOT1") (SEQ ID NO: 3). Blue columns are for the operated, ischemic leg; red columns are for the unoperated, contralateral leg.
Figure 16:
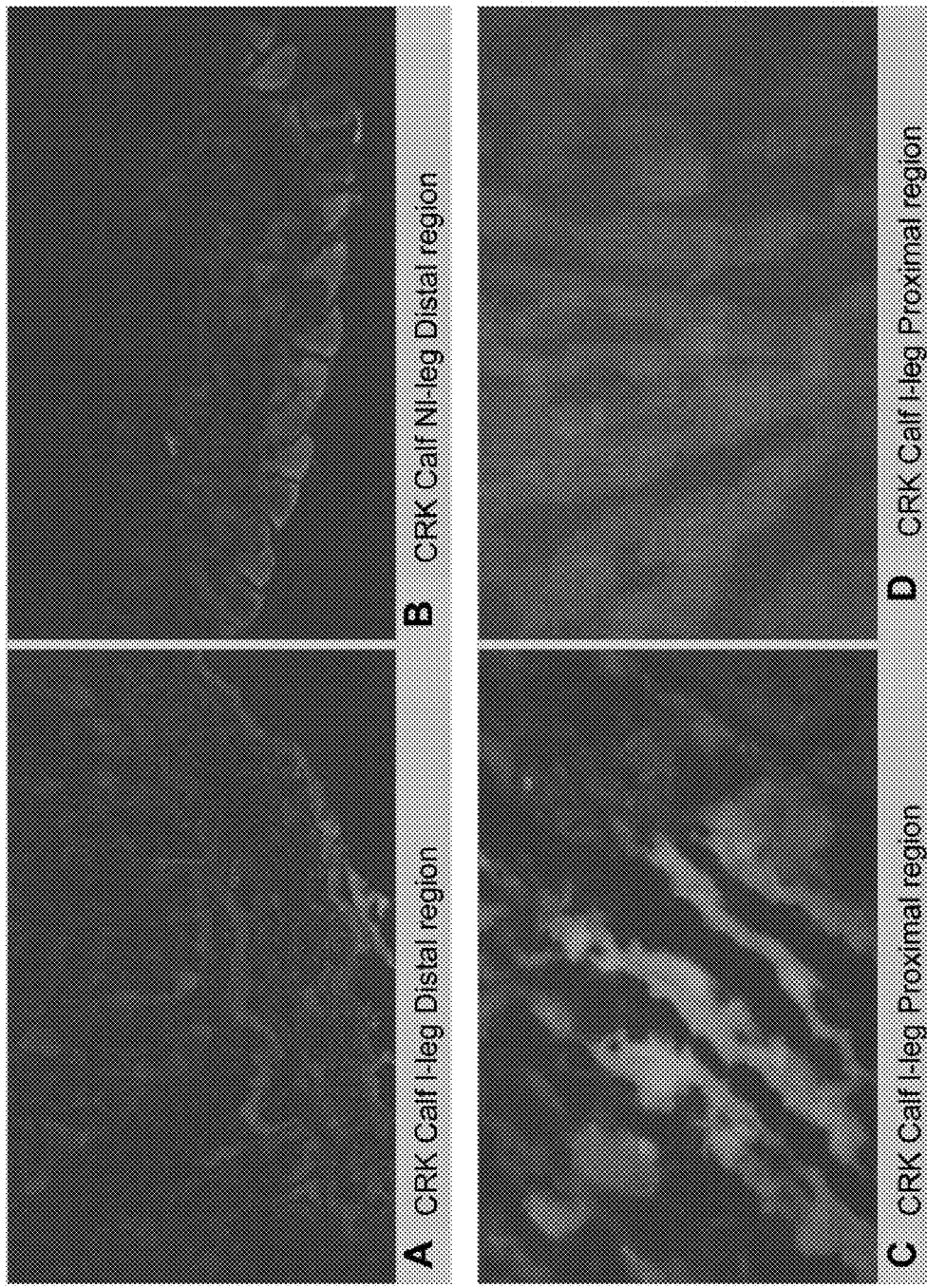
FIG. 16 illustrates typical cryosections demonstrating homing of CRK and Clot1 peptides in the mouse ischemic hindlimb. 16A demonstrates homing of CRK peptides in the mouse ischemic calf ischemic leg distal region. 16B demonstrates homing of CRK peptides in the mouse calf non-ischemic leg distal region. 16C demonstrates homing of CRK peptides in the mouse calf ischemic leg proximal region. 16D demonstrates homing of CRK peptides in the mouse calf non-ischemic leg proximal region.
Figure 17:
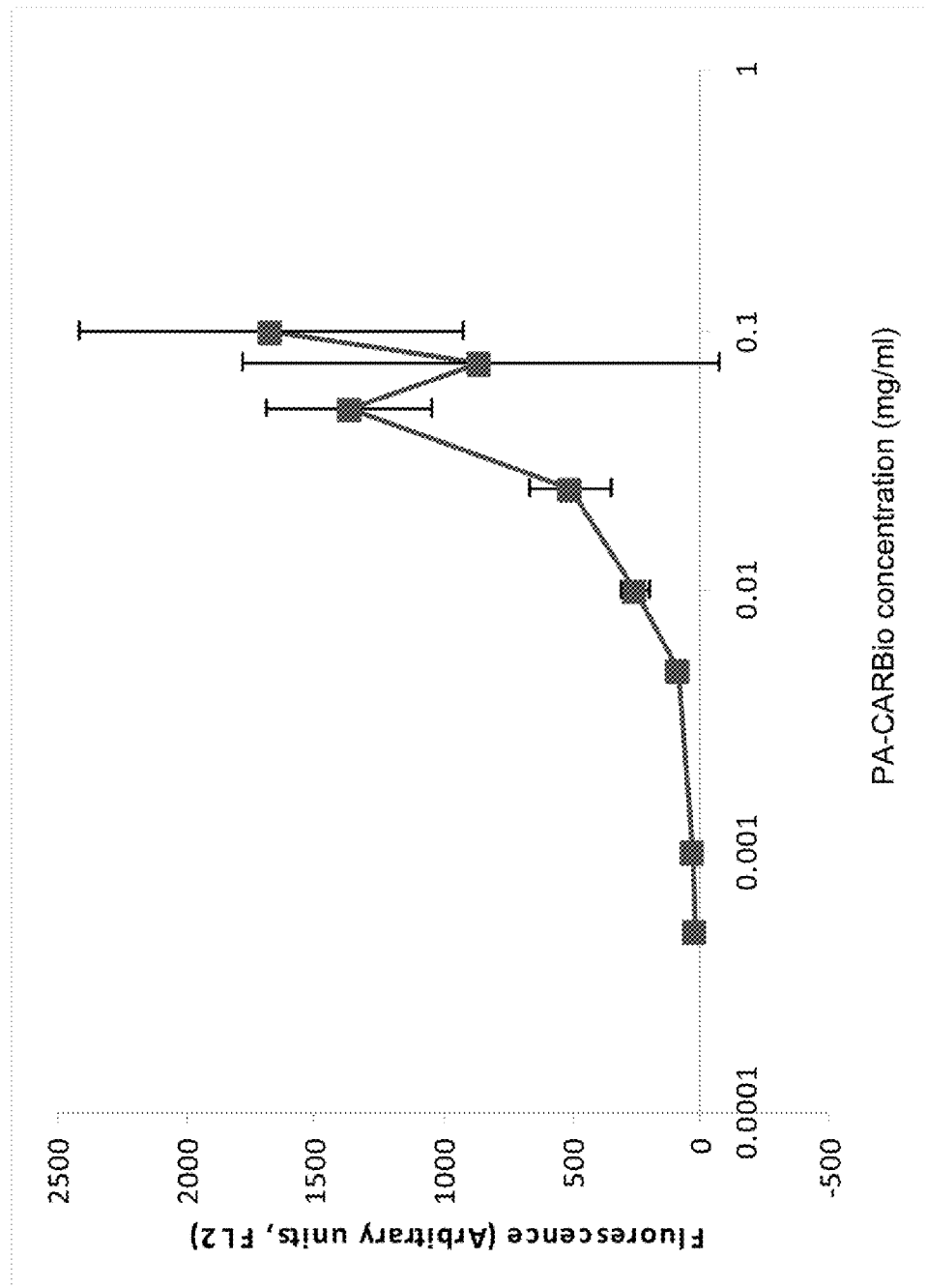
FIG. 17 illustrates PA-BioCAR (SEQ ID NO: 28) uptake assessed by FLOW detection of fluorescent marker.
Figure 18:
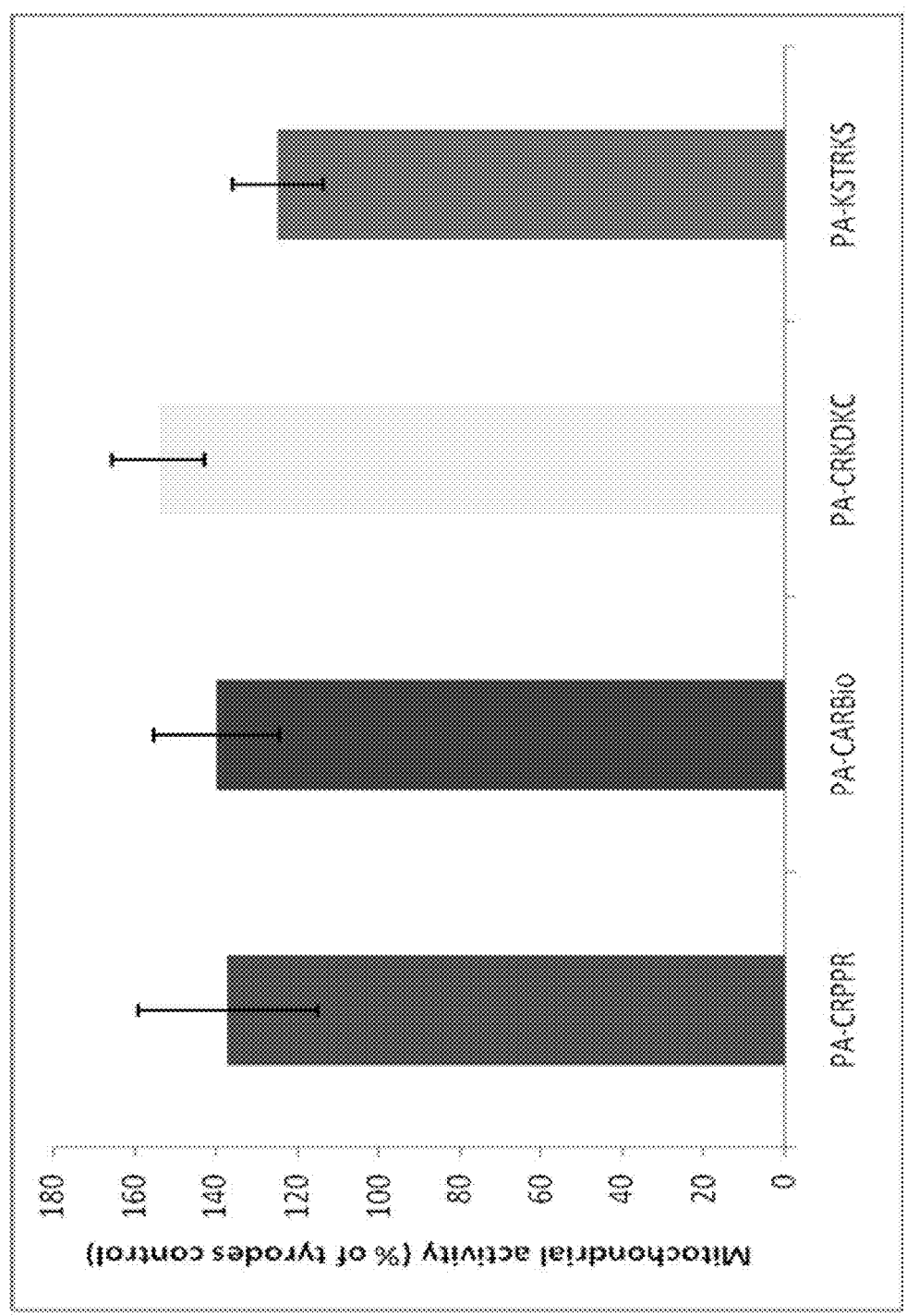
FIG. 18 is an assessment of cell viability via mitochondrial activity (MTT) assay performed on cells 12 hours after standard coating regimen at varied concentrations of palmitated peptide. Data are mean value±SD for 1 experiment with 12 samples in each group.
Figure 19:
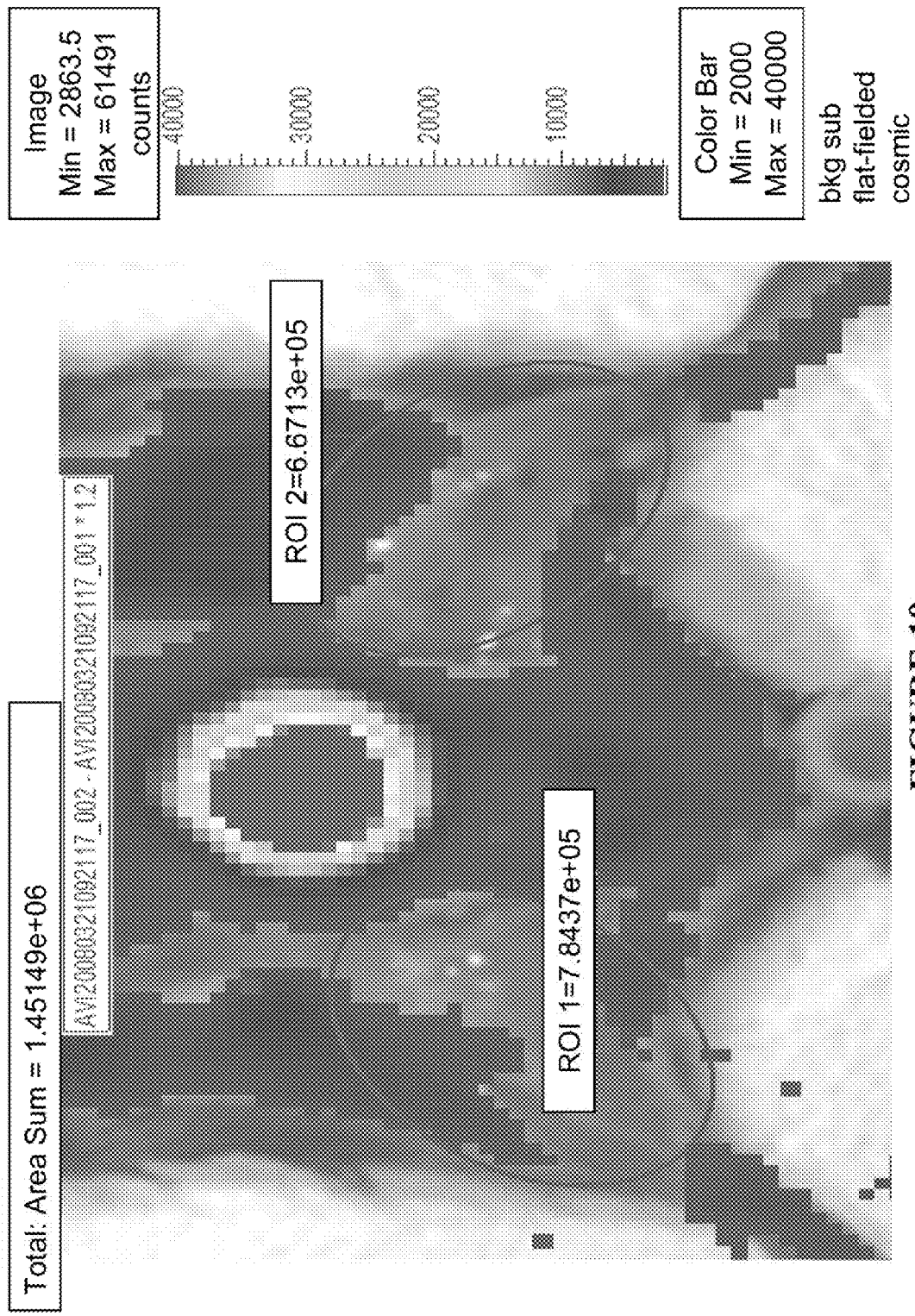
FIG. 19 illustrates Xenogen image of mouse after 2 h circulation of PA-KSTRKS coated hMSCs.
Figure 20:
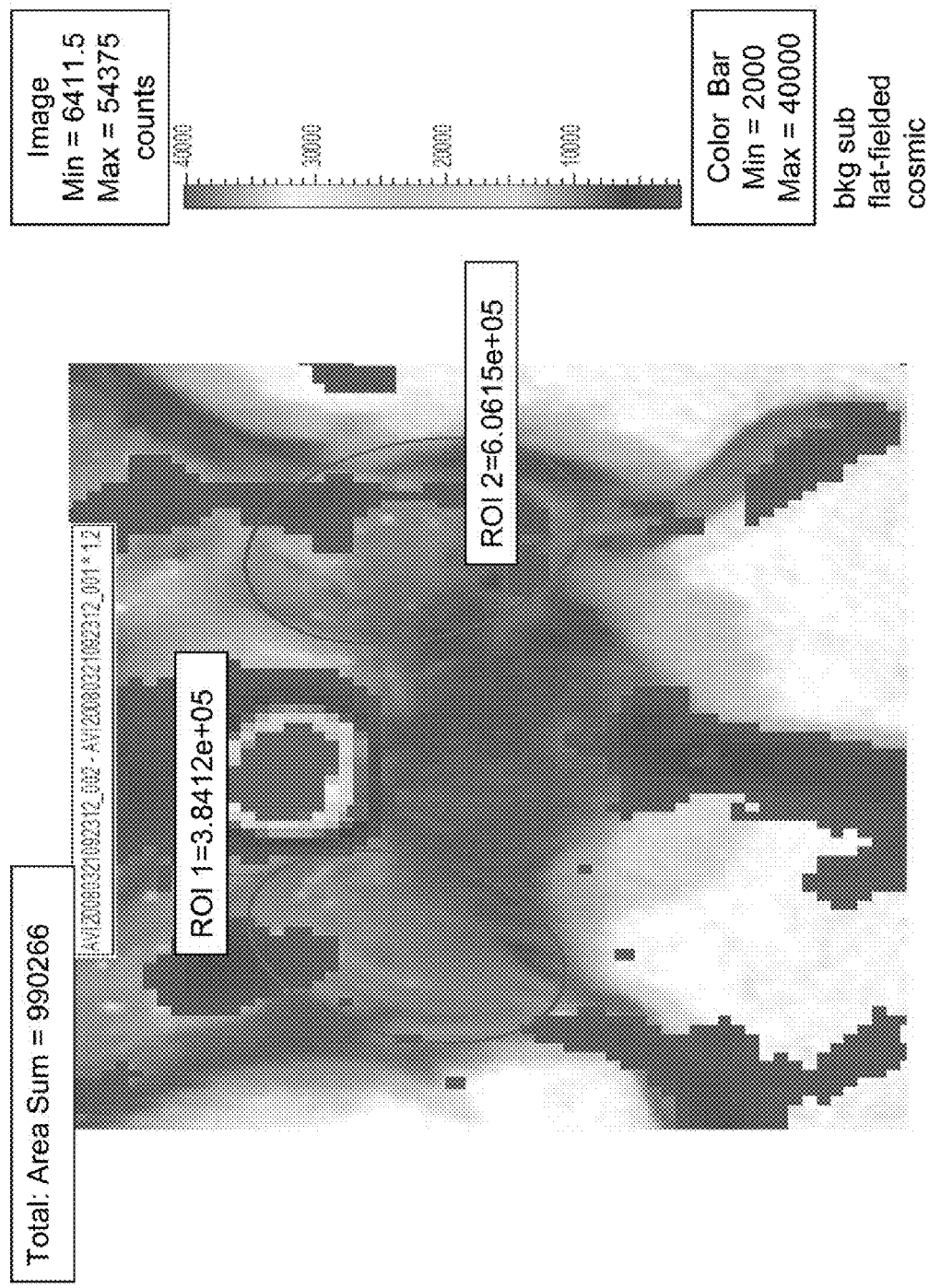
FIG. 20 illustrates Xenogen image of mouse after 2 h circulation of PA-BioCAR coated hMSCs.
Figure 21:
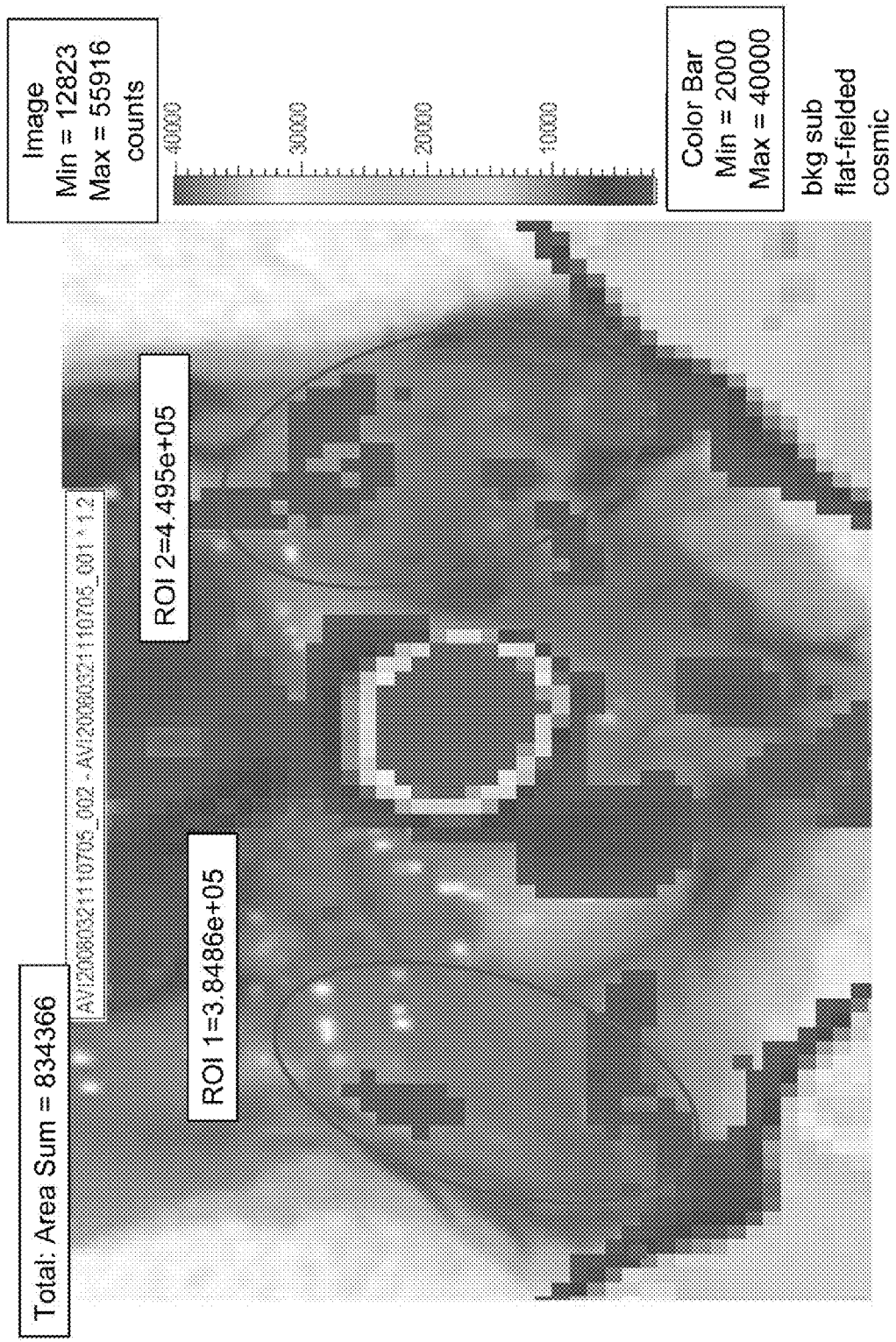
FIG. 21 illustrates Xenogen image of mouse after 2 h circulation of hMSC with no peptide coating.
Figure 23:
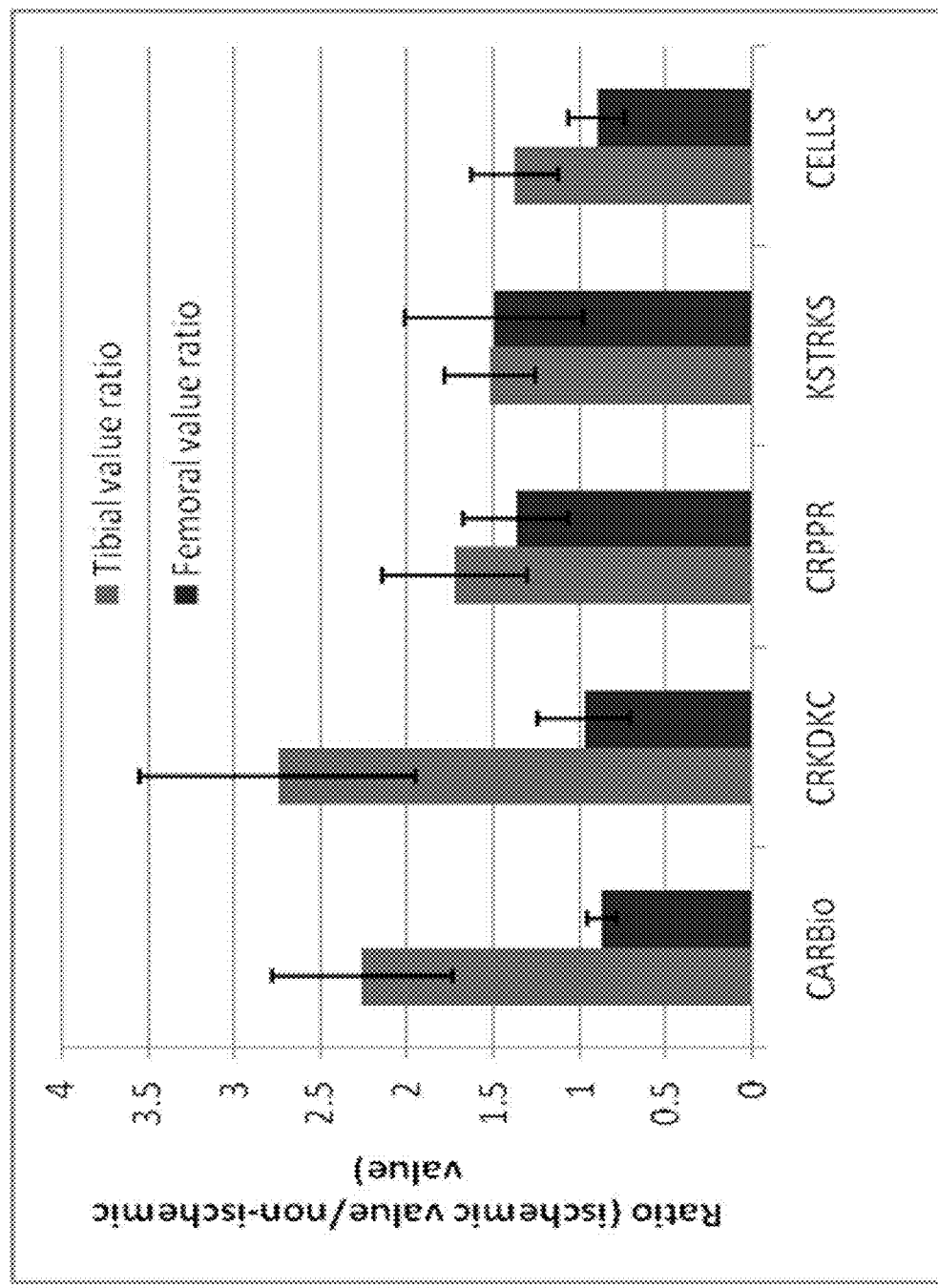
FIG. 23 illustrates a summary of the Means of the Ratio of Cell Densities observed in the tibial (calf) and femoral (thigh) sections of the ischemic and non-ischemic legs. Mean±SEM for N≥10.

RESULTS: Fluorescent-peptide homing and phage homing were observed in the mouse hindlimb ischemia model (FIGS. 15-16). Saturation of cell surfaces with a model palmitated peptide (PA-BioCAR) was demonstrated with an optimal coating concentration of 0.05 mg peptide/mL (FIG. 17). Retention of cell viability after coating with all peptides was observed. (FIG. 18) Increased (40%) homing of uncoated MSCs to the ischemic tibial sections was observed, compared to the contralateral non-ischemic tibial tissue control. No corresponding homing to the femoral tissue was observed for native MSCs. See FIG. 22. Increased homing of peptide-coated MSCs, compared to uncoated MSCs was observed to the ischemic tibial sections for two of the peptides: 2.3-fold higher for PA-BioCAR coated MSCs and 2.7-fold higher for PA-CRKDKC-coated MSCs (FIGS. 19-21). Significantly higher levels of cell homing was observed to the tibial sections of ischemic tissues than to the femoral sections of the same legs for most peptides tested (FIG. 23).

The apparent distributions of the cells with the different ligands may indicate that embodiments of the invention could be used in conjunction on the cells (multiple peptides per cell), or cells with different coatings could be mixed to achieve additive or synergistic localization.

Although the present invention has been described in considerable detail with reference to certain preferred embodiments thereof, other versions are possible. Therefore the spirit and scope of the appended claims should not be limited to the description and the preferred versions contained within this specification.

The invention claimed is:

1. A targeting complex comprising:
a heart homing peptide, CRPPR (SEQ ID NO: 1);
a palmitate moiety, linked to the amino terminus of a spacer comprising amino acids chosen from NKS and NSK wherein
the spacer covalently links the homing peptide to the lipid moiety and further comprising a cell.

2. The targeting complex of claim 1, wherein the homing molecule selectively homes to vasculature.

3. A coated cell comprising:
a cell; and
a plurality of targeting complexes coating the cell;
each of said targeting complexes comprising:
a heart homing peptide, CRPPR (SEQ ID NO: 1);
a palmitate moiety linked to the amino terminus of a spacer comprising amino acids chosen from NKS and NSK and to the cell; wherein
the spacer covalently links the homing peptide to the palmitate moiety.

4. The coated cell of claim 3, wherein the lipid moiety is non-covalently attached to the cell.

5. The coated cell of claim 3, wherein the lipid moiety is integrated into a lipid bilayer of a cell membrane of the cell.

6. The coated cell of claim 3, wherein the lipid moiety intercalates into a lipid bilayer of a cell membrane of the cell.

7. The coated cell of claim 3, wherein the targeting complex is present on the surface of the cell at a concentration of from about 0.001 µM to about 1 mM.

8. A pharmaceutical composition comprising:
a cell;
a plurality of targeting complexes coating the cell;
each of said targeting complexes comprising:
a heart homing peptide, CRPPR (SEQ ID NO: 1);
a palmitate moiety linked to the amino terminus of a spacer comprising amino acids chosen from NKS and NSK;

wherein the spacer covalently links the homing peptide to the palmitate moiety; and a pharmaceutically acceptable carrier.

9. The pharmaceutical composition of claim 8, wherein the lipid moiety is non-covalently attached to the cell.

10. The pharmaceutical composition of claim 8, wherein the lipid moiety is integrated into a lipid bilayer of a cell membrane of the cell.

11. The pharmaceutical composition of claim 8, wherein the lipid moiety intercalates into a lipid bilayer of a cell membrane of the cell.

12. The targeting complex of claim 1, wherein the cell is a multi-potent progenitor cell.

13. The targeting complex of claim 1, wherein the cell is a mesenchymal stem cell.

14. The targeting complex of claim 1, wherein the cell is a hematopoietic stem cell.

15. The coated cell of claim 3, wherein the cell is a multi-potent progenitor cell.

16. The coated cell of claim 3, wherein the cell is a mesenchymal stem cell.

17. The coated cell of claim 3, wherein the cell is a hematopoietic stem cell.

18. The pharmaceutical composition of claim 8, wherein the cell is a multipotent progenitor cell.

19. The pharmaceutical composition of claim 8, wherein the cell is a mesenchymal stem cell.

20. The pharmaceutical composition of claim 8, wherein the cell is a hematopoietic stem cell.

* * * * *

SEQUENCE LISTING

```
<160> NUMBER OF SEQ ID NOS: 28

<210> SEQ ID NO 1
<211> LENGTH: 5
<212> TYPE: PRT
<213> ORGANISM: Artificial Sequence
<220> FEATURE:
<223> OTHER INFORMATION: Targeting Sequence 1

<400> SEQUENCE: 1

Cys Arg Pro Pro Arg
1               5

<210> SEQ ID NO 2
<211> LENGTH: 9
<212> TYPE: PRT
<213> ORGANISM: Artificial Sequence
<220> FEATURE:
<223> OTHER INFORMATION: Trageting Sequence 2
```

<400> SEQUENCE: 2

Cys Arg Arg Glu Thr Ala Trp Ala Cys
1               5

<210> SEQ ID NO 3
<211> LENGTH: 10
<212> TYPE: PRT
<213> ORGANISM: Artificial Sequence
<220> FEATURE:
<223> OTHER INFORMATION: Targeting Sequence 3

<400> SEQUENCE: 3

Cys Gly Leu Ile Ile Gln Lys Asn Glu Cys
1               5                   10

<210> SEQ ID NO 4
<211> LENGTH: 10
<212> TYPE: PRT
<213> ORGANISM: Artificial Sequence
<220> FEATURE:
<223> OTHER INFORMATION: Targeting Sequence 4

<400> SEQUENCE: 4

Cys Asn Ala Gly Glu Ser Ser Lys Asn Cys
1               5                   10

<210> SEQ ID NO 5
<211> LENGTH: 9
<212> TYPE: PRT
<213> ORGANISM: Artificial Sequence
<220> FEATURE:
<223> OTHER INFORMATION: Targeting Sequence 5

<400> SEQUENCE: 5

Cys Ala Arg Ser Lys Asn Lys Asp Cys
1               5

<210> SEQ ID NO 6
<211> LENGTH: 6
<212> TYPE: PRT
<213> ORGANISM: Artificial Sequence
<220> FEATURE:
<223> OTHER INFORMATION: Targeting Sequence 6

<400> SEQUENCE: 6

Cys Arg Lys Asp Lys Cys
1               5

<210> SEQ ID NO 7
<211> LENGTH: 65
<212> TYPE: PRT
<213> ORGANISM: Homo sapiens

<400> SEQUENCE: 7

Lys Pro Gly Leu Asn Gly Leu Ser Ser Ala Asp Pro Ser Ser Asp Trp
1               5                   10                  15

Asn Ala Pro Ala Glu Glu Trp Gly Asn Trp Val Asp Glu Asp Arg Ala
                20                  25                  30

Ser Leu Leu Lys Ser Gln Glu Pro Ile Ser Asn Asp Gln Lys Val Ser
            35                  40                  45

Asp Asp Asp Lys Glu Lys Gly Glu Gly Ala Leu Pro Thr Gly Lys Ser
        50                  55                  60

Lys
65

```
<210> SEQ ID NO 8
<211> LENGTH: 5
<212> TYPE: PRT
<213> ORGANISM: Artificial Sequence
<220> FEATURE:
<223> OTHER INFORMATION: Targeting Sequence 8

<400> SEQUENCE: 8

Cys Arg Glu Lys Ala
1               5

<210> SEQ ID NO 9
<211> LENGTH: 5
<212> TYPE: PRT
<213> ORGANISM: Artificial Sequence
<220> FEATURE:
<223> OTHER INFORMATION: Targeting Sequence 9

<400> SEQUENCE: 9

Cys Gly Lys Arg Lys
1               5

<210> SEQ ID NO 10
<211> LENGTH: 9
<212> TYPE: PRT
<213> ORGANISM: Artificial Sequence
<220> FEATURE:
<223> OTHER INFORMATION: Targeting Sequence 10

<400> SEQUENCE: 10

Cys Ala Pro Gly Pro Ser Lys Ser Cys
1               5

<210> SEQ ID NO 11
<211> LENGTH: 8
<212> TYPE: PRT
<213> ORGANISM: Artificial Sequence
<220> FEATURE:
<223> OTHER INFORMATION: Targeting Sequence 11

<400> SEQUENCE: 11

Gly Arg Pro Ala Arg Pro Ala Arg
1               5

<210> SEQ ID NO 12
<211> LENGTH: 9
<212> TYPE: PRT
<213> ORGANISM: Artificial Sequence
<220> FEATURE:
<223> OTHER INFORMATION: Targeting Sequence 12

<400> SEQUENCE: 12

Cys Gly Gly Gly Gly Gly Gly Gly Cys
1               5

<210> SEQ ID NO 13
<211> LENGTH: 20
<212> TYPE: DNA
<213> ORGANISM: Artificial Sequence
<220> FEATURE:
<223> OTHER INFORMATION: Primer 1

<400> SEQUENCE: 13
aacccctcaa gacccgttta                                              20

<210> SEQ ID NO 14
```

```
<211> LENGTH: 6
<212> TYPE: PRT
<213> ORGANISM: Artificial Sequence
<220> FEATURE:
<223> OTHER INFORMATION: Targeting Sequence 14

<400> SEQUENCE: 14

Lys Ser Thr Arg Lys Ser
1               5

<210> SEQ ID NO 15
<211> LENGTH: 7
<212> TYPE: PRT
<213> ORGANISM: Artificial Sequence
<220> FEATURE:
<223> OTHER INFORMATION: Targeting Sequence 15

<400> SEQUENCE: 15

Arg Ile Gly Arg Val Leu Lys
1               5

<210> SEQ ID NO 16
<211> LENGTH: 6
<212> TYPE: PRT
<213> ORGANISM: Artificial Sequence
<220> FEATURE:
<223> OTHER INFORMATION: Targeting Sequence 16

<400> SEQUENCE: 16

Ser Lys Leu Gly Phe Phe
1               5

<210> SEQ ID NO 17
<211> LENGTH: 7
<212> TYPE: PRT
<213> ORGANISM: Artificial Sequence
<220> FEATURE:
<223> OTHER INFORMATION: Targeting Sequence 17

<400> SEQUENCE: 17

Gly Gly Gly Val Phe Trp Gln
1               5

<210> SEQ ID NO 18
<211> LENGTH: 7
<212> TYPE: PRT
<213> ORGANISM: Artificial Sequence
<220> FEATURE:
<223> OTHER INFORMATION: Targeting Sequence 18

<400> SEQUENCE: 18

His Gly Arg Val Arg Pro His
1               5

<210> SEQ ID NO 19
<211> LENGTH: 7
<212> TYPE: PRT
<213> ORGANISM: Artificial Sequence
<220> FEATURE:
<223> OTHER INFORMATION: Targeting Sequence 19

<400> SEQUENCE: 19

Val Val Leu Val Thr Ser Ser
1               5

<210> SEQ ID NO 20
<211> LENGTH: 8
<212> TYPE: PRT
```

```
<213> ORGANISM: Artificial Sequence
<220> FEATURE:
<223> OTHER INFORMATION: Targeting Sequence 20

<400> SEQUENCE: 20

Cys Leu His Arg Gly Asn Ser Cys
1               5

<210> SEQ ID NO 21
<211> LENGTH: 12
<212> TYPE: PRT
<213> ORGANISM: Artificial Sequence
<220> FEATURE:
<223> OTHER INFORMATION: Targeting Sequence 21

<400> SEQUENCE: 21

Cys Arg Ser Trp Asn Lys Ala Asp Asn Arg Ser Cys
1               5                   10

<210> SEQ ID NO 22
<211> LENGTH: 6
<212> TYPE: PRT
<213> ORGANISM: Artificial Sequence
<220> FEATURE:
<223> OTHER INFORMATION: Targeting Sequence 22

<400> SEQUENCE: 22

Cys Ala Arg Pro Ala Arg
1               5

<210> SEQ ID NO 23
<211> LENGTH: 6
<212> TYPE: PRT
<213> ORGANISM: Artificial Sequence
<220> FEATURE:
<223> OTHER INFORMATION: Targeting Sequence 23

<400> SEQUENCE: 23

Cys Pro Lys Arg Pro Arg
1               5

<210> SEQ ID NO 24
<211> LENGTH: 20
<212> TYPE: DNA
<213> ORGANISM: Artificial Sequence
<220> FEATURE:
<223> OTHER INFORMATION: Primer 2

<400> SEQUENCE: 24
agcggaccag attatcgcta                                            20

<210> SEQ ID NO 25
<211> LENGTH: 6
<212> TYPE: PRT
<213> ORGANISM: Artificial Sequence
<220> FEATURE:
<223> OTHER INFORMATION: Lipid Modified Peptide 1
<220> FEATURE:
<221> NAME/KEY: LIPID
<222> LOCATION: (1)..(1)
<223> OTHER INFORMATION: PALMITATE via amide bond

<400> SEQUENCE: 25

Lys Ser Thr Arg Lys Ser
1               5

<210> SEQ ID NO 26
<211> LENGTH: 5
```

```
<212> TYPE: PRT
<213> ORGANISM: Artificial Sequence
<220> FEATURE:
<223> OTHER INFORMATION: Lipid Modified Peptide 2
<220> FEATURE:
<221> NAME/KEY: LIPID
<222> LOCATION: (1)..(1)
<223> OTHER INFORMATION: PALMITATE via amide bond

<400> SEQUENCE: 26

Cys Arg Pro Pro Arg
1               5

<210> SEQ ID NO 27
<211> LENGTH: 6
<212> TYPE: PRT
<213> ORGANISM: Artificial Sequence
<220> FEATURE:
<223> OTHER INFORMATION: Lipid Modified Peptide 3
<220> FEATURE:
<221> NAME/KEY: LIPID
<222> LOCATION: (1)..(1)
<223> OTHER INFORMATION: PALMITATE via amide bond
<220> FEATURE:
<221> NAME/KEY: DISULFID
<222> LOCATION: (1)..(6)

<400> SEQUENCE: 27

Cys Arg Lys Asp Lys Cys
1               5

<210> SEQ ID NO 28
<211> LENGTH: 13
<212> TYPE: PRT
<213> ORGANISM: Artificial Sequence
<220> FEATURE:
<223> OTHER INFORMATION: Lipid Modified Peptide 4
<220> FEATURE:
<221> NAME/KEY: LIPID
<222> LOCATION: (1)..(1)
<223> OTHER INFORMATION: PALMITATE via amide bond
<220> FEATURE:
<221> NAME/KEY: MOD_RES
<222> LOCATION: (2)..(2)
<223> OTHER INFORMATION: Biotinylation
<220> FEATURE:
<221> NAME/KEY: DISULFID
<222> LOCATION: (5)..(13)

<400> SEQUENCE: 28

Ser Lys Asn Ser Cys Ala Arg Ser Lys Asn Lys Asp Cys
1               5                   10
```